United States Patent
Tsurumoto et al.

(10) Patent No.: US 11,053,217 B2
(45) Date of Patent: Jul. 6, 2021

(54) OPTICALLY ACTIVE PYRROLIDINE COMPOUND AND METHOD FOR PRODUCING SAME

(71) Applicant: MITSUBISHI TANABE PHARMA CORPORATION, Osaka (JP)

(72) Inventors: Joji Tsurumoto, Osaka (JP); Kenji Morokuma, Osaka (JP)

(73) Assignee: MITSUBISHI TANABE PHARMA CORPORATION, Osaka (JP)

(*) Notice: Subject to any disclaimer, the term of this patent is extended or adjusted under 35 U.S.C. 154(b) by 0 days.

(21) Appl. No.: 16/651,049

(22) PCT Filed: Sep. 28, 2018

(86) PCT No.: PCT/JP2018/036225
§ 371 (c)(1),
(2) Date: Mar. 26, 2020

(87) PCT Pub. No.: WO2019/065954
PCT Pub. Date: Apr. 4, 2019

(65) Prior Publication Data
US 2020/0239440 A1 Jul. 30, 2020

(30) Foreign Application Priority Data

Sep. 29, 2017 (JP) .............................. JP2017-190331

(51) Int. Cl.
*C07D 401/14* (2006.01)

(52) U.S. Cl.
CPC ................. *C07D 401/14* (2013.01)

(58) Field of Classification Search
None
See application file for complete search history.

(56) References Cited

U.S. PATENT DOCUMENTS

| | | | |
|---|---|---|---|
| 5,618,949 A | 4/1997 | Ma et al. | |
| 6,258,833 B1 | 7/2001 | Martins et al. | |
| 6,294,561 B1 | 9/2001 | Fowler et al. | |
| 6,376,489 B1 | 4/2002 | Martins et al. | |
| 6,423,710 B1 | 7/2002 | Martins et al. | |
| 6,458,787 B1 | 10/2002 | Martins et al. | |
| 2002/0032224 A1 | 3/2002 | Fowler et al. | |
| 2004/0023945 A1 | 2/2004 | Martins et al. | |
| 2004/0152754 A1 | 8/2004 | Martins et al. | |
| 2006/0074123 A1 | 4/2006 | Martins et al. | |
| 2013/0338140 A1 | 12/2013 | Blake et al. | |
| 2016/0280682 A1 | 9/2016 | Allen et al. | |
| 2016/0297758 A1 | 10/2016 | Allen et al. | |
| 2016/0297796 A1 | 10/2016 | Allen et al. | |
| 2017/0190697 A1 | 7/2017 | Yamamoto et al. | |
| 2017/0240512 A1 | 8/2017 | Yukimasa et al. | |
| 2018/0179182 A1 | 6/2018 | Allen et al. | |
| 2018/0258076 A1 | 9/2018 | Sato et al. | |
| 2019/0062282 A1 | 2/2019 | Yukimasa et al. | |

FOREIGN PATENT DOCUMENTS

| | | |
|---|---|---|
| JP | 2017-105765 A | 6/2017 |
| WO | WO 01/47879 A1 | 7/2001 |
| WO | WO 01/47905 A1 | 7/2001 |
| WO | WO 01/47914 A1 | 7/2001 |
| WO | WO 2012/118850 A1 | 9/2012 |
| WO | WO 2014/078323 A1 | 5/2014 |
| WO | WO 2014/078372 A1 | 5/2014 |
| WO | WO 2014/078378 A1 | 5/2014 |
| WO | WO 2015/182723 A1 | 12/2015 |
| WO | WO 2016/021629 A1 | 2/2016 |
| WO | WO 2017/090743 A1 | 6/2017 |

OTHER PUBLICATIONS

Arena et al., "Concise Synthesis (+)-allo-Kainic Acid via MgI$_2$-Mediated Tandem Aziridine Ring Opening—Formal [3+2] Cycloaddition," Organic Letters (2013), vol. 15, No. 16, pp. 4250-4253.
International Preliminary Report on Patentablity and Written Opinion dated Mar. 31, 2020, in PCT/JP2018/036225.
International Search Report dated Dec. 28, 2018, in PCT/JP2018/036225.
Karlsson et al., "trans-3,4-Disubstituted pyrrolines by 1,3-dipolar cycloaddition: enantioselective approaches and their limitations," Tetrahedron: Asymmetry (1999), vol. 10, pp. 2605-2616.
Ma et al., "Asymmetric dipolar cycloaddition reactions: a practical, convergent synthesis of chiral pyrrolidines," Tetrahedron: Asymmetry (1997), vol. 8, No. 6, pp. 883-887.
Nichols et al., "Preparation of Pyrrolidine-Based PDE4 Inhibitors via Enantioselective Conjugate Addition of α-Substituted Malonates to Aromatic Nitroalkenes," Organic Letters (2006), vol. 8, No. 7, pp. 1495-1498.
Extended European Search Report for European Application No. 18860623.0, dated Dec. 21, 2020.

*Primary Examiner* — Zinna Northington Davis
(74) *Attorney, Agent, or Firm* — Birch, Stewart, Kolasch & Birch, LLP

(57) ABSTRACT

The present invention provides: a methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid which is represented by formula (1) and is excellent in crystallinity; and a method for producing the same; and a production intermediate thereof; and a production method using this compound.

5 Claims, 1 Drawing Sheet

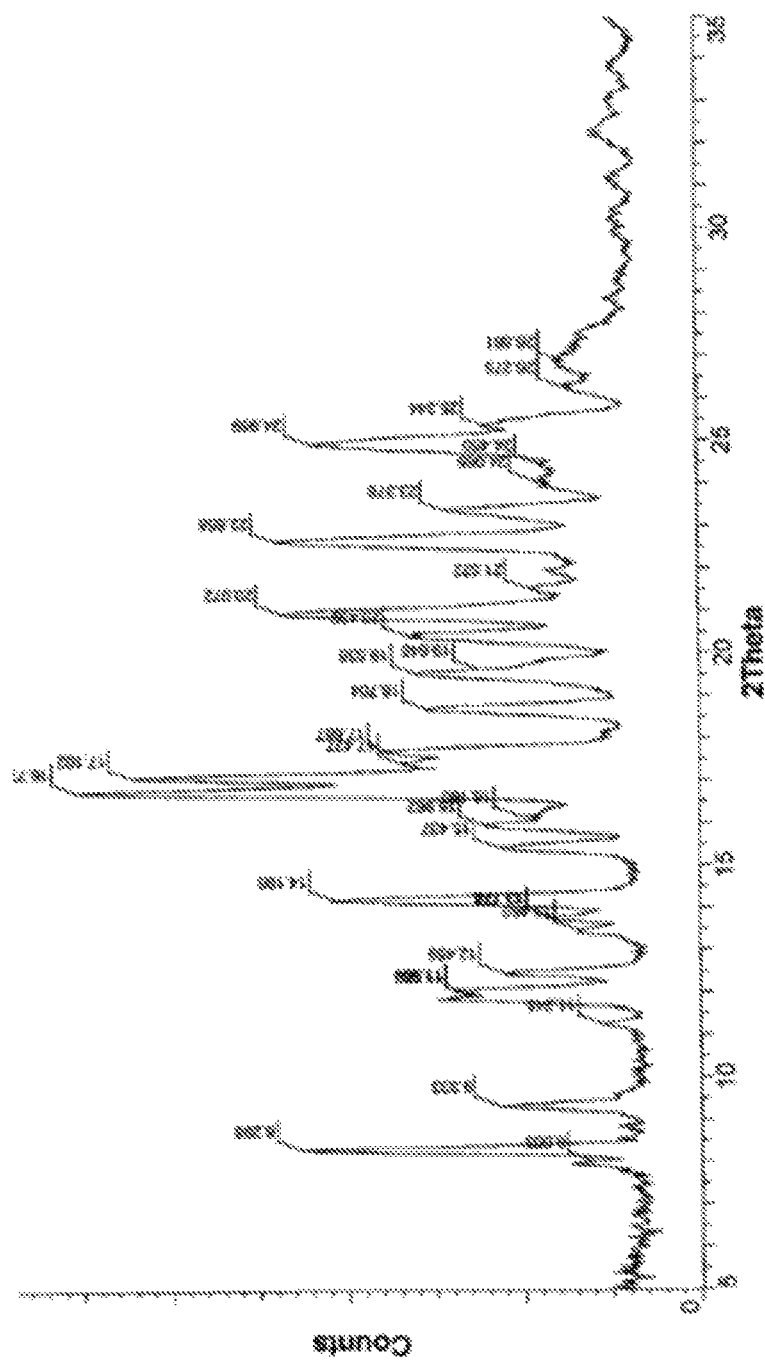

OPTICALLY ACTIVE PYRROLIDINE COMPOUND AND METHOD FOR PRODUCING SAME

TECHNICAL FIELD

The present invention relates to methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid, which has excellent crystallinity (hereinafter, referred to as "Present compound" or "compound of the present invention"), a method for preparing the same, and a production intermediate thereof, as well as a method for production of a particular product using the same.

BACKGROUND ART

The Patent Document 1 describes compounds which has melanocortin receptor activation activity and is useful for prophylaxis or treatment of various diseases or conditions in which an activation of melanocortin receptor is involved, and a method for preparing the compounds, and also describes dihydrochloride salts of a compound represented by formula (11) below in Example 19.

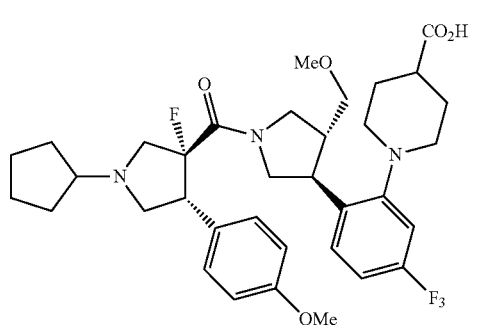

However, the Patent Document 1 doesn't disclose specifically the compounds described herein including the above-mentioned present compound, and the method for preparing these compounds.

Also the Patent Documents 2 to 9 and non-Patent Documents 1 to 3 describe a method for preparing optically active pyrrolidine derivatives by a cyclization reaction of styrene derivatives with the tertiary amine using 4-phenyl-2-oxazolidinone as an asymmetric auxiliary group. However, a cyclization reaction of styrene derivatives with the tertiary amine as described in the present application isn't described.

CITATION LIST

Patent Document

Patent Document 1: WO 2015/182723
Patent Document 2: WO 2001/047879
Patent Document 3: WO 2001/047905
Patent Document 4: WO 2001/047914
Patent Document 5: WO 2012/118850
Patent Document 6: WO 2014/078372
Patent Document 7: WO 2014/078378
Patent Document 8: WO 2014/078323
Patent Document 9: WO 2016/021629

Non-Patent Document

Non-Patent Document 1: Tetrahedron: Asymmetry 1997, Vol. 8, No. 6, 883-887
Non-Patent Document 2: Tetrahedron: Asymmetry 1999, Vol. 10, 2605-2616
Non-Patent Document 3: Organic Letters 2006, Vol. 8, No. 7, 1495-1498

SUMMARY OF THE INVENTION

Problems to be Solved by Invention

In a preparation of an active pharmaceutical ingredient, a strict quality control of intermediate compounds, etc., is required as the end of the overall steps is being approached, and there is thus a need to always get a consistent quality of compound. Accordingly, if an intermediate compound can be obtained in a crystal form, it is possible to isolate and purify by a processing operation with easy operability such as crystallization and recrystallization, which is preferable in aspects of a quality control. Compounds having excellent crystallinity also have an advantage in that accurate weighing is possible.

The purpose of the present invention is to provide salts of methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate, which has excellent crystallinity, and a method showing excellent stereoselectivity for preparing the compound.

Means to Solve Problems

The present invention includes the followings [1] to [11], however, which are not limited thereto.

[1] Methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid, which is represented by formula (1):

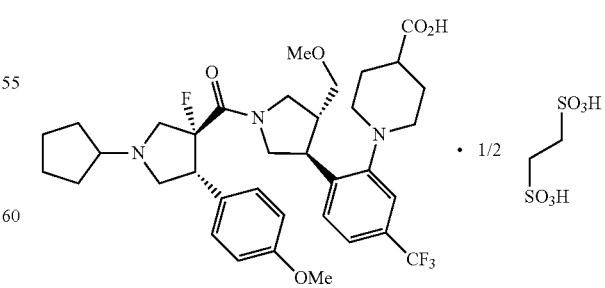

[1-2] A crystal of the compound according to [1] which has as a diffraction angle (2θ±0.2°) diffraction peaks of at least 8.298, 14.198, 16.776, 17.102, 20.972, 22.658, 24.959.

[2] A method for preparing the compound (1), which is shown by the reaction scheme:

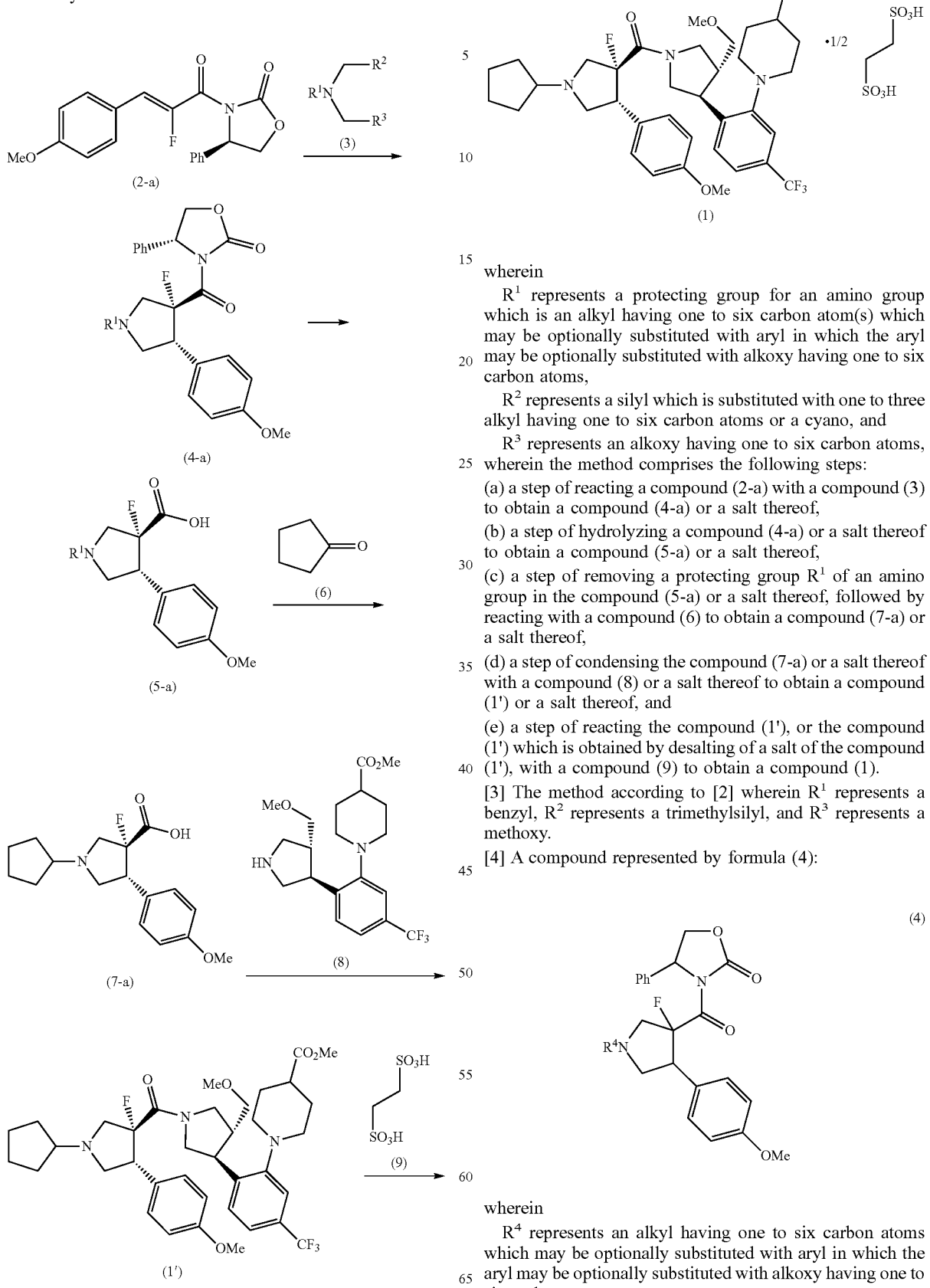

wherein
$R^1$ represents a protecting group for an amino group which is an alkyl having one to six carbon atom(s) which may be optionally substituted with aryl in which the aryl may be optionally substituted with alkoxy having one to six carbon atoms,
$R^2$ represents a silyl which is substituted with one to three alkyl having one to six carbon atoms or a cyano, and
$R^3$ represents an alkoxy having one to six carbon atoms, wherein the method comprises the following steps:

(a) a step of reacting a compound (2-a) with a compound (3) to obtain a compound (4-a) or a salt thereof,
(b) a step of hydrolyzing a compound (4-a) or a salt thereof to obtain a compound (5-a) or a salt thereof,
(c) a step of removing a protecting group $R^1$ of an amino group in the compound (5-a) or a salt thereof, followed by reacting with a compound (6) to obtain a compound (7-a) or a salt thereof,
(d) a step of condensing the compound (7-a) or a salt thereof with a compound (8) or a salt thereof to obtain a compound (1') or a salt thereof, and
(e) a step of reacting the compound (1'), or the compound (1') which is obtained by desalting of a salt of the compound (1'), with a compound (9) to obtain a compound (1).

[3] The method according to [2] wherein $R^1$ represents a benzyl, $R^2$ represents a trimethylsilyl, and $R^3$ represents a methoxy.

[4] A compound represented by formula (4):

wherein
$R^4$ represents an alkyl having one to six carbon atoms which may be optionally substituted with aryl in which the aryl may be optionally substituted with alkoxy having one to six carbon atoms,
or salts thereof.

[5] A compound represented by formula (4-a):

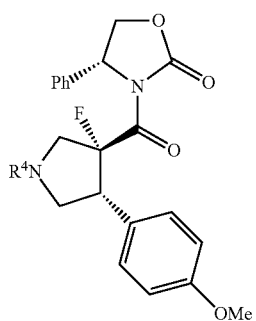

wherein the symbols are the same as defined in [4], or salts thereof.

[6] A compound represented by formula (5):

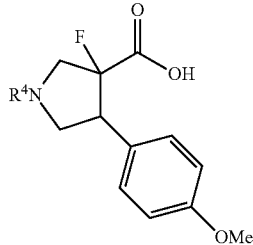

wherein
R⁵ represents an alkyl having one to six carbon atoms which may be optionally substituted with aryl in which the aryl may be optionally substituted with alkoxy having one to six carbon atoms,
or salts thereof.

[7] A compound represented by formula (5-a):

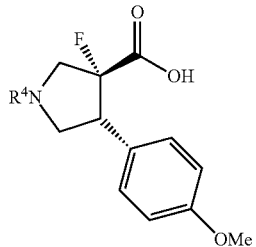

wherein the symbol is the same as defined in [6], or salts thereof.

[8] A compound represented by formula (2):

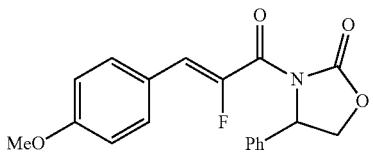

or salts thereof.

[9] A compound represented by formula (2-a):

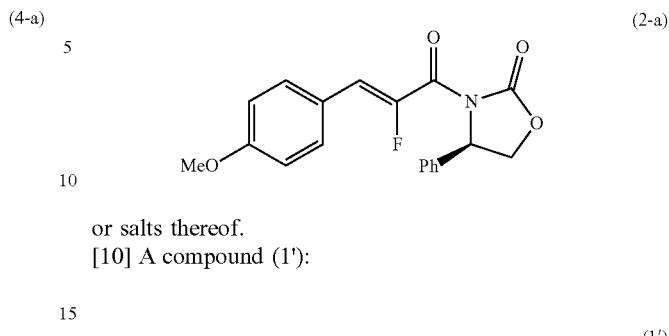

or salts thereof.

[10] A compound (1'):

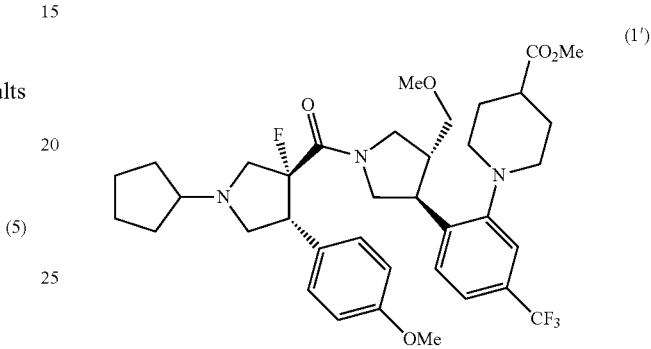

or salts thereof.

[11] A method for preparing a compound represented by formula (11):

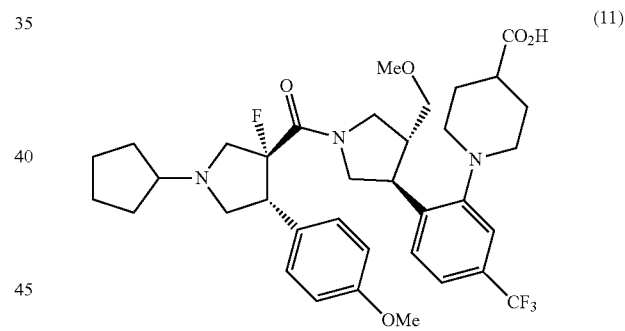

or pharmaceutically acceptable salts thereof, which comprises
a step of hydrolyzing methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid or salts thereof, and optionally, as needed, a step of subjecting to a salt-forming treatment.

In [11], as methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid, those obtained by the method according to [2] or [3] is preferably used.

Effect of Invention

The present invention can provide methyl 1-{2-[(3S,4R)-1-[(3R,4R)-1-cyclopentyl-3-fluoro-4-(4-methoxyphenyl)

pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid, which has excellent crystallinity. Further, the present invention can provide a method showing excellent stereoselectivity for preparing the same compound, and a production intermediate compound of the same compound, and a method using the same compound for preparing compounds which is useful for prophylaxis or treatment of various diseases or conditions in which an activation of melanocortin receptor is involved.

BRIEF DESCRIPTION OF DRAWINGS

FIG. 1 shows a powder X-ray diffraction pattern of methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid which is obtained by Example 7.

MODE FOR CARRYING OUT THE INVENTION

The definition of each group described herein can be freely combined as desired, unless otherwise specified.

As used herein, the "alkyl having one to six carbon atom(s)" refers to a straight or branched saturated hydrocarbon chain group having one to six carbon atom(s) ($C_{1-6}$). Alkyl having one to four carbon atom(s) ($C_{1-4}$) is particularly preferable. Specific examples thereof include methyl, ethyl, n-propyl, i-propyl, n-butyl, i-butyl, t-butyl, 2-methyl-n-butyl, i-amyl (i.e., 3-methyl-n-butyl), and 2-methyl-n-pentyl and the others. Preferable specific examples thereof include methyl, ethyl, n-propyl, i-propyl, n-butyl, i-butyl and t-butyl.

As used herein, the "alkoxy having one to six carbon atom(s)" refers to a monovalent group in which the above-described alkyl group having one to six carbon atom(s) is attached to an oxygen atom, for example, a straight or branched alky-O— having one to six carbon atom(s) ($C_{1-6}$), and alky-O— having one to four carbon atom(s) ($C_{1-4}$) is particularly preferable. Specific examples thereof include methoxy, ethoxy, n-propoxy, i-propoxy, n-butoxy, i-butoxy, t-butoxy, 2-methyl-n-butoxy, i-amyloxy (i.e., 3-methyl-n-butoxy), 2-methyl-n-pentoxy and the others. Preferable specific examples thereof include methoxy, ethoxy, n-propoxy, i-propoxy, n-butoxy, i-butoxy, t-butoxy.

As used herein, the "aryl" refers to six to ten membered monocyclic aromatic hydrocarbon group or fused bicyclic aromatic hydrocarbon group. Specific examples of the monocyclic aromatic hydrocarbon group include phenyl and the others, and specific examples of the fused bicyclic aromatic hydrocarbon group include naphthyl and the others.

As used herein, the "salt-forming treatment" refers to a treatment for forming a salt of compound (including a pharmaceutically acceptable salt) with the corresponding acid. Examples of the corresponding acids include inorganic acids (such as hydrochloric acid, sulfuric acid, phosphoric acid, hydrobromic acid, and the others); and organic acids (such as acetic acid, oxalic acid, malonic acid, 2-methylmalonic acid, succinic acid, fumaric acid, maleic acid, malic acid, tartaric acid, dibenzoyl tartaric acid, citric acid, methanesulfonic acid, benzenesulfonic acid, ethanedisulfonic acid, tosylic acid and the others).

As used herein, examples of "salt(s) of compound" include inorganic acid salts (such as hydrochloride salt, sulfate, phosphate, hydrobromide salt and the others); and organic acid salts (such as acetate, oxalate, malonate, 2-methylmalonate, succinate, fumarate, malenate, malate, tartrate, dibenzoyltartrate, citrate, methanesulfonate, benzenesulfonate, ethanedisulfonate, tosylate and the others).

As used herein, examples of "pharmaceutically acceptable salt(s)" include inorganic acid salts (such as hydrochloride salt, sulfate salt, phosphate salt, hydrobromide salt and the others); and organic acid salts (such as acetate, fumarate, oxalate, citrate, methanesulfonate, benzenesulfonate, tosylate, malenate and the others).

Embodiment

In the present invention, preferable aspects are described below.

$R^1$, $R^4$ and $R^5$ may be a protecting group of amino group which is stable in the presence of acid, and includes specifically, an alkyl having one to six carbon atoms which may be optionally substituted with aryl in which the aryl may be optionally substituted with alkoxy having one to six carbon atoms, and includes preferably an alkyl group having one to six carbon atoms, a benzyl or 1-phenethyl each of which may be optionally substituted with alkoxy having one to six carbon atoms, and more preferably, methyl, ethyl, benzyl, p-methoxybenzyl and 1-phenethyl, and particularly preferably, benzyl.

Examples of "alkyl having one to six carbon atoms" in the term of "alkyl having one to six carbon atoms which may be optionally substituted with aryl in which the aryl may be optionally substituted with alkoxy having one to six carbon atoms" for $R^1$, $R^4$ and $R^5$ include preferably methyl and ethyl, and more preferably methyl.

Examples of "aryl" in the term of "alkyl having one to six carbon atoms which may be optionally substituted with aryl in which the aryl may be optionally substituted with alkoxy having one to six carbon atoms" for $R^1$, $R^4$ and $R^5$ include preferably phenyl.

Examples of "alkoxy having one to six carbon atoms" in the term of "alkyl having one to six carbon atoms which may be optionally substituted with aryl in which the aryl may be optionally substituted with alkoxy having one to six carbon atoms" for $R^1$, $R^4$ and $R^5$ include preferably methoxy.

Examples of $R^2$ include a silyl which may be optionally substituted with one to three of alkyl having one to six carbon atom(s), or a cyano, and include preferably trialkylsilyl or cyano, more preferably trimethylsilyl or cyano, and particularly trimethylsilyl.

Examples of $R^3$ include an alkoxy having one to six carbon atoms, and preferably methoxy.

As one aspect of the present invention, a method comprising at least one steps selected from the following preparation steps (A) to (F) is included.
(A) a step of reacting a compound represented by formula (2-a) with a compound represented by formula (3) to prepare a compound represented by formula (4-a) (or salts thereof)

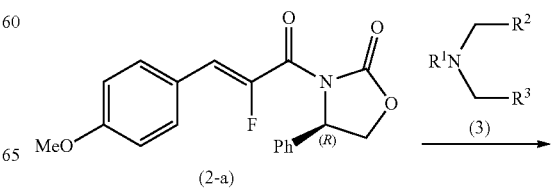

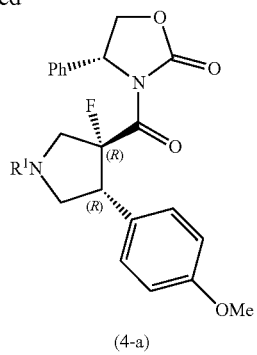

(4-a)

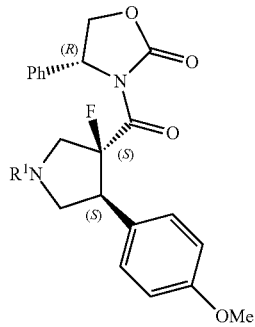

(4-b)

wherein $R^1$, $R^2$ and $R^3$ are the same as defined above.

A reaction of the compound represented by formula (2-a) with the compound represented by formula (3) can be conducted in the presence of an appropriate catalyst in an appropriate solvent.

The catalyst may be any substances for providing proton, and includes for example, acids (such as inorganic acids or organic acids), and includes preferably, trifluoroacetic acid and trichloroacetic acid, and more preferably trifluoroacetic acid. Alternatively, the catalyst may be any substances for providing fluoride ion, and includes for example, tetrabutylammonium fluoride.

A solvent may be anything that does not disturb the reaction, and examples thereof include ethers (such as tetrahydrofuran, 1,4-dioxane, 1,2-dimethoxyethane, 1,1-diethoxypropane, 1,1-dimethoxymethane, 2,2-dimethoxypropane); halogenated aromatic hydrocarbons (such as chlorobenzene); halogenated aliphatic hydrocarbons (such as chloroform, 1,2-dichloroethene and dichloromethane); acetonitrile, dimethylformamide; and mixture of two or more of these solvents.

A reaction temperature of the present reaction is varied depending on used reagent(s) or used reaction condition (for example, used solvent(s)), and is usually under cooling to under heating, preferably 0 to 40° C., and more preferably 25° C.

A reaction period of the present reaction is varied depending on used reagent(s) or used reaction condition (for example, used solvent(s)), and is usually from 30 minutes to 2 hours, and preferably 1 hour.

Also the mixed amount of the compound represented by formula (3) is within a range of usually 1 to 3 molar equivalent(s) and preferably 1.8 molar equivalents, as opposed to 1 mole equivalent of the compound represented by formula (2).

The mixed ratio of the catalyst to the compound of formula (2) is within the range of usually 0.01 to 1 molar equivalent(s), and preferably 0.1 molar equivalents.

The present reaction may be conducted under inert gas, for example, under nitrogen gas or argon gas.

In the reaction of the compound represented by formula (2-a) with the compound represented by formula (3), the following compound (hereinafter, referred to as compound represented by formula (4-b)) may be obtained as a by-product. The compound represented by formula (4-a) and the compound represented by formula (4-b) have diastereomeric relationships to each other.

wherein $R^1$ is the same as defined above.

Examples of the method for separating the compound represented by formula (4-a) and the compound represented by formula (4-b) include crystallization, recrystallization, chroromatography and the others, and two or more thereof may be combined.

Specific examples of crystallization method includes a method in which a mixture of the compound represented by formula (4-a) and the compound represented by formula (4-b) is dissolved in ethers (such as 1,2-dimethoxyethane, tetrahydrofuran, 1,4-dioxane, 1,1-diethoxypropane, 1,1-diethoxymethane and 2,2-dimethoxypropane); halogenated aromatic hydrocarbons (such as chlorobenzene); or halogenated aliphatic hydrocarbons (such as chloroform, 1,2-dichloroethene and dichloromethane), and then alcohols (such as methanol, ethanol, 1-propanol, 2-propanol, 1-butanol, 2-butanol, 3-methyl-1-butanol, 2-methyl-1-propanol and 1-pentanol); or ketones (such as acetone) is then added thereto. Preferable examples of the method include a method in which a mixture of the compound represented by formula (4-a) and the compound represented by formula (4-b) is dissolved in 1,2-dimethoxyethane, and methanol is then added thereto.

(B) a step for preparing a compound represented by formula (5-a) (or salts thereof) from the compound represented by formula (4-a) (or salts thereof)

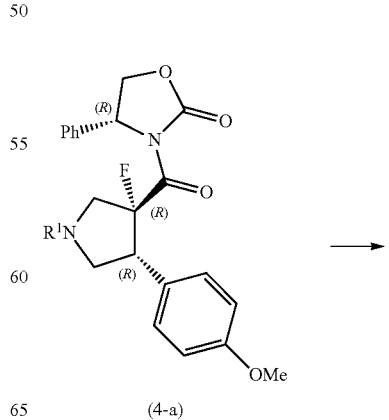

(4-a)

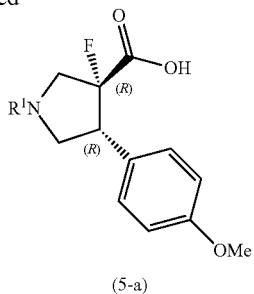

(5-a)

wherein, R¹ is the same as defined above.

In the reaction for obtaining the compound represented by formula (5-a) from the compound represented by formula (4-a), the following compound represented by formula (5-b) may be obtained as a by-product. The compound represented by formula (5-a) and the compound represented by formula (5-b) have enantiomeric relationships to each other.

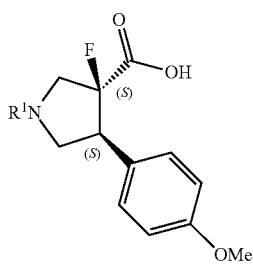

(5-b)

wherein R¹ is the same as defined above.

Examples of a method for separating the compound represented by formula (5-a) and the compound represented by formula (5-b) include an optical resolution (such as crystallization, recrystallization and chromatography), and two or more thereof may be combined.

The compound represented by formula (5-a) (or salts thereof) may be obtained by hydrolyzing the compound represented by formula (4-a) (or salts thereof) in an appropriate solvent.

A solvent may be anything that does not disturb the present reaction, and examples of the solvent include alcohols (such as methanol, ethanol, 1-propanol, 2-propanol, 1-butanol, 2-butanol, 3-methyl-1-butanol, 2-methyl-1-propanol and 1-pentanol); ketones (such as acetone, methyl ethyl ketone, methyl isopropyl ketone, methyl butyl ketone and methyl isobutyl ketone); ethers (such as 1,2-dimethoxyethane, 1,4-dioxane, 1,1-dimethoxymethane and methyltetrahydrofuran); amides (such as N,N-dimethylformamide and N,N-dimethylacetamide); N-methylpyrrolidone, acetonitrile and dimethylsulfoxide; and mixtures of two or more of these solvents.

Preferable examples of hydrolysis include a hydrolysis in the presence of a base.

Examples of the base include inorganic bases (such as lithium hydroxide, sodium hydroxide and potassium hydroxide).

A reaction temperature of the present reaction is varied depending on used reagent(s) or used reaction condition (for example, used solvent(s)), and is usually under cooling to under heating, preferably 0 to 30° C., and more preferably 0° C.

A reaction period of the present reaction is varied depending on used reagent(s) or used reaction condition (for example, used solvent(s)), and is usually from 1 hour to 6 hours, and preferably 3 hours.

Also the additive amount of the base is within a range of 1 to 2 molar equivalent(s) and preferably 1.2 molar equivalents, as opposed to 1 mole equivalent of the compound represented by formula (4-a).

The present reaction may be conducted under inert gas, for example, under nitrogen gas or argon gas.

(C) a step for reacting the compound represented by formula (5-a) (or salts thereof) with a compound represented by formula (6) to prepare a compound represented by formula (7-a)

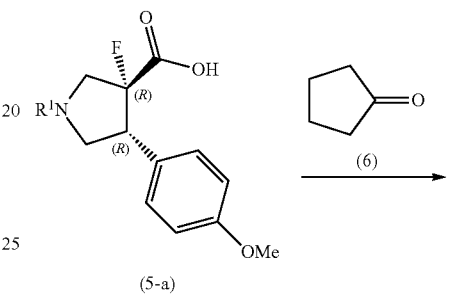

(5-a)

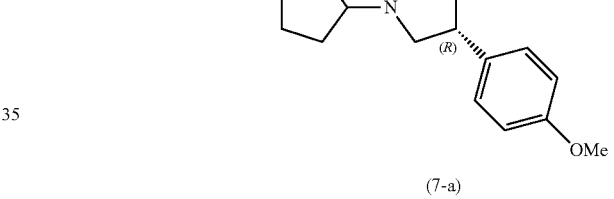

(7-a)

wherein R¹ is the same as defined above.

The compound represented by formula (7-a) can be obtained by reacting the compound represented by formula (5-a) with the compound represented by formula (6) in the presence of an appropriate reductive agent in an appropriate solvent In the reaction of the compound represented by formula (5-a) with the compound represented by formula (6), the following compound represented by formula (7-b) may be obtained as a by-product. The compound represented by formula (7-a) and the compound represented by formula (7-b) have enantiomeric relationships to each other.

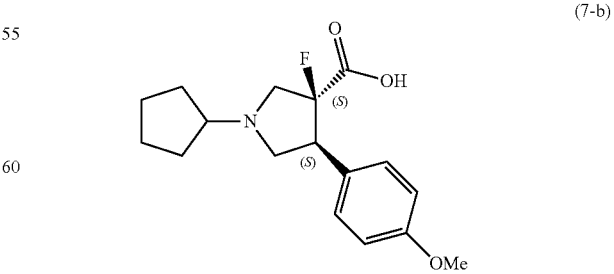

(7-b)

Examples of a method for separating the compound represented by formula (7-a) and the compound represented by formula (7-b) include optical resolution (such as crystallization, recrystallization and chromatography), and two or more thereof may be combined.

Examples of the reductive agent include a combination of a transition metal selected from nickel, palladium, rhodium, platinum or ruthenium, and a hydrogen source such as hydrogen gas. The transition metals include simple substances of metal, or metals supported on carriers (such as carbon (such as activated carbon), zeolite, alumina, and silica gel). Preferable examples of the transition metals include palladium. Preferable examples of the carriers include carbon.

A solvent may be anything that does not disturb the present reaction, and examples of the solvent include alcohols (such as methanol, ethanol, 1-propanol, 2-propanol, 1-butanol, 2-butanol, 3-methyl-1-butanol, 2-methyl-1-propanol and 1-pentanol); ethers (such as 1,2-dimethoxyethane, 1,4-dioxane, 1,1-diethoxypropane, 1,1-dimethoxymethane, 2,2-dimethoxypropane, tetrahydrofuran and methyltetrahydrofuran), and mixtures of two or more thereof.

A reaction temperature of the present reaction is varied depending on used reagent(s) or used reaction condition (for example, used solvent(s)), and is usually under cooling to under heating, preferably 40 to 60° C., and more preferably 50° C.

A reaction period of the present reaction is varied depending on used reagent(s) or used reaction condition (for example, used solvent(s)), and is usually from 3 hours to 24 hours, and preferably 20 hours.

Also the additive amount of the reducing agent is within a range of 0.01 to 0.1 molar equivalents and preferably 0.016 molar equivalents, as opposed to 1 mole equivalent of the compound represented by formula (5-a).

Also the mixed amounts of the compound represented by formula (6) is within a range of usually 1 to 5 molar equivalent(s) and preferably 2.6 molar equivalents, as opposed to 1 molar equivalent of the compound represented by formula (5-a).

(D) a step of reacting the compound represented by formula (7-a) (or salts thereof) with a compound represented by formula (8) (or salts thereof) to prepare a compound represented by formula (1') (or salts thereof)

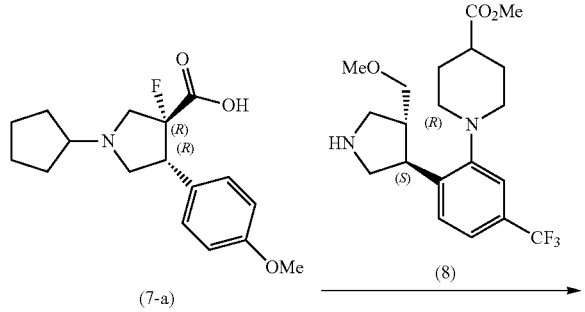

-continued

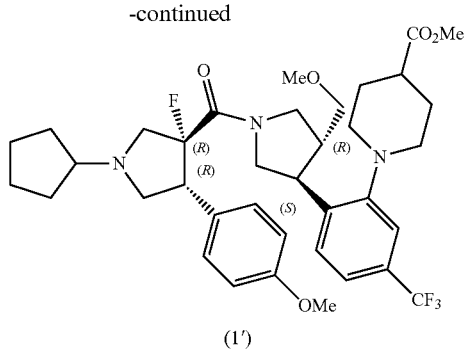

The compound represented by formula (1') can be obtained by subjecting to a condensation reaction of the compound represented by formula (7-a) with the compound represented by formula (8) in the presence of an appropriate base and an appropriate condensation agent in an appropriate solvent.

Examples of the base include amines (such as diisopropylethylamine and triethylamine), and preferably diisopropylethylamine or triethylamine, and more preferably diisopropylethylamine.

Examples of the condensation agent include alkylphosphonic acid anhydrides (such as propylphoshonic acid anhydride); carbodiimides (such as N,N'-dicyclohexyl carbodiimide, 1-ethyl-3-(3-dimethylaminopropyl)carbodiimide hydrochloride salt, and 1,1'-carbonyldiimidazole), and preferably propylphosphonic acid anhydride.

A solvent may be anything that does not disturb the present reaction, and examples of the solvent include aromatic hydrocarbons (such as toluene); hydrogenated aromatic hydrocarbons (such as chlorobenzene); halogenated aliphatic hydrocarbons (such as chloroform, 1,2-dichloroethene and dichloromethane); ethers (such as t-butyl methyl ether and diethyl ether); esters (such as ethyl acetate, isobutyl acetate, isopropyl acetate, propyl acetate and n-butyl acetate); acetonitrile; and mixtures of two or more thereof.

A reaction temperature of the present reaction is varied depending on used reagent(s) or used reaction condition (for example, used solvent(s)), and is usually under cooling to under heating, preferably 0 to 30° C., and more preferably 10° C.

A reaction period of the present reaction is varied depending on used reagent(s) or used reaction condition (for example, used solvent(s)), and is usually from 3 hours to 24 hours, and preferably 13 hours.

Also the additive amount of the base is within a range of usually 2 to 5 molar equivalent(s) and preferably 3.5 molar equivalents, as opposed to 1 mole equivalent of the compound represented by formula (7-a).

Also the additive amount of the condensation agent is within a range of usually 1 to 2 molar equivalent(s) and preferably 1.5 molar equivalents, as opposed to 1 mole equivalent of the compound represented by formula (7-a).

Further the mixed amount of the compound represented by formula (8) is within a range of usually 1 to 1.2 molar equivalent(s) and preferably 1.05 molar equivalents, as opposed to 1 mole equivalent of the compound represented by formula (7-a).

(E) a step of reacting the compound represented by formula (1') (or salts thereof) with a compound represented by formula (9) to prepare a compound represented by formula (1)

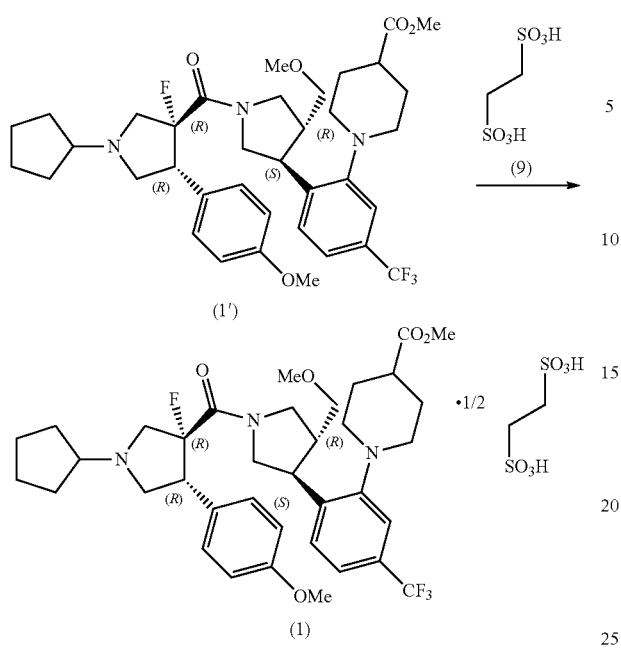
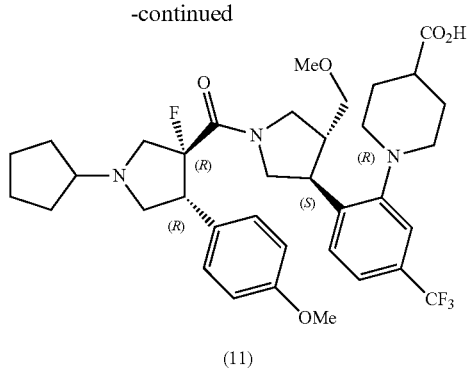

The compound represented by formula (1) can be obtained by reacting the compound represented by formula (1') with a compound represented by formula (9) under an appropriate condition.

The compound represented by formula (1) can be obtained in a crystalline form by crystalizing it in alcohols. Examples of the alcohols include preferably alcohols (such as methanol, ethanol, 1-propanol, 2-propanol, n-butyl alcohol, isobutyl alcohol and t-butyl alcohol), more preferably ethanol and isopropanol, and particularly preferably isopropanol.

A reaction temperature of the present reaction is varied depending on used reaction condition (for example, used solvent(s)), and is preferably 50 to 85° C., and more preferably 75° C.

A reaction period of the present reaction is varied depending on used reaction condition (for example, used solvent(s)), and is usually from 1 hour to 5 hours, and preferably 1 hour.

The additive amount of the compound (9) as opposed to that of the compound (1') is within a range of usually 0.5 to 0.6 molar equivalents, and preferably 0.5 molar equivalents.

(F) a step for preparing a compound represented by formula (11) from the compound represented by formula (1)

Formula (11)

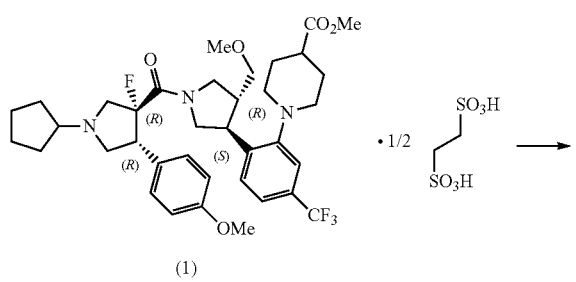

The compound represented by formula (11) can be obtained by as needed, subjecting salts of the compound represented by formula (1) to a desalting treatment, followed by hydrolyzing the resulting product in an appropriate solvent.

A solvent may be anything that does not disturb the present reaction, and examples of the solvents include alcohols (such as methanol, ethanol, 1-propanol, isopropanol, 1-butanol, 2-butanol, 3-methyl-1-butanol, 2-methyl-1-propanol and 1-pentanol); ethers (such as tetrahydrofuran, methyltetrahydrofuran, 1,4-dioxane, 1,2-dimethoxyethane and 1,1-dimethoxymethane); ketones (such as acetone, methyl ethyl ketone, methyl butyl ketone, methyl isobutyl ketone and methyl isopropyl ketone); amides (such as N,N-dimethylacetamide and N,N-dimethylformamide); dimethylsulfoxide, N-methylpyrrolidone and acetonitrile; and mixtures of two or more thereof.

Preferable examples of the hydrolysis include a hydrolysis in the presence of a base.

Examples of the base include inorganic bases (such as lithium hydroxide, sodium hydroxide and potassium hydroxide).

A reaction temperature of the present reaction is varied depending on used reaction condition (for example, used solvent(s)), and is usually under cooling to under heating, preferably 10 to 45° C., and more preferably 40° C.

A reaction period of the present reaction is varied depending on used reaction condition (for example, used solvent(s)), and is usually from 3 to 8 hours, and preferably 4 hours or 5 hours and more preferably 5 hours.

Also an additive amount of the base as opposed to 1 molar equivalent of the compound represented by formula (1) is within a range of 1 to 2 molar equivalent(s), preferably 1.1 or 1.5 molar equivalents, and more preferably 1.1 molar equivalents.

EXAMPLES

Hereinafter, the present invention is explained in more detail by using the following Preparation Examples and Examples and the like, however, the present invention should not be limited to these examples.

As used herein, "Me" refers to methyl, "Et" refers to ethyl, "Ph" refers to phenyl, "Bn" refers to benzyl, and "TMS" refers to trimethylsilyl.

Example 1

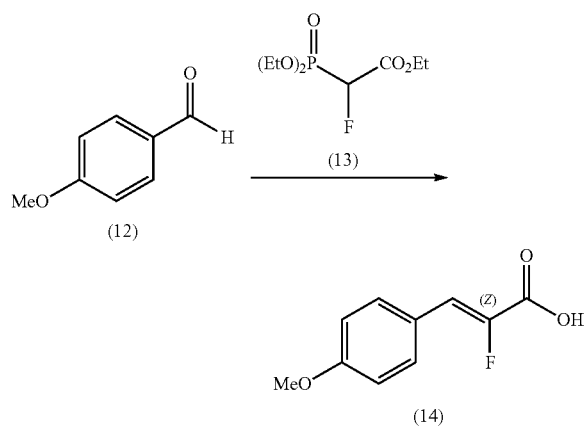

To a solution of the compound (13) (65.0 kg) in tetrahydrofuran (108.0 kg) were added diazabicycloundecene (40.8 kg) and tetrahydrofuran (13.4 kg) while stirring the solution at room temperature. The compound (12) (30.4 kg) and tetrahydrofuran (13.4 kg) were added thereto at 10° C., the reaction mixture was then stirred at room temperature for 21 hours. Ethanol (119.8 kg) and 7.4% aqueous sodium hydroxide solution (358.2 kg) were added thereto at room temperature, and the mixture was stirred for 2 hours. Water (137.7 kg), 35% hydrochloric acid (69.0 kg) and water (15.2 kg) were added thereto in that order at room temperature, and the mixture was stirred at room temperature for 30 minutes and at 0° C. for 1 hour. The crystals were collected by filtration, and washed with a mixed solution of ethanol (24.0 kg) and water (60.9 kg), and further with water (151.9 kg). The crystals were dried at 60° C. or less to obtain the compound (14) (28.6 kg) (yield 65%). MS (ESI): m/z 195.1 [M−H]−

Example 2

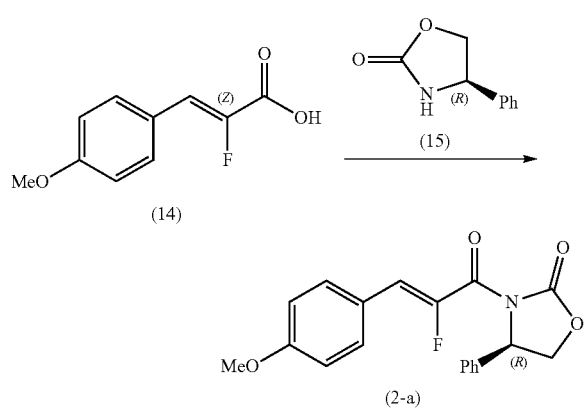

To a mixture solution of the compound (14) (28.4 kg) in 1,2-dimethoxyethane (124.4 kg) and N,N-dimethylformamide (1.06 kg) were added at 55° C. thionyl chloride (20.8 kg) and 1,2-dimethoxyethane (24.7 kg), and the mixture was stirred for 2 hours. The mixture was cooled to room temperature, and lithium chloride (6.76 kg), the compound (15) (23.6 kg) and 1,2-dimethoxyethane (24.8 kg) were added thereto in that order, and the mixture was raised to 55° C. N,N-diisopropylethylamine (46.8 kg) and 1,2-dimethoxyethane (24.7 kg) were added thereto, and the mixture was stirred at 55° C. for 4 hours and at room temperature for 9 hours. The mixed solution of methanol (22.4 kg) and water (114.2 kg) was added thereto at room temperature, and the mixture was stirred at room temperature for 30 minutes. The crystals were collected by filtration, and the crystals were washed with a mixed solution of water (28.4 kg) and 1,2-dimethoxyethane (49.4 kg). The crystals were dried at 60° C. or less to obtain the compound (2-a) (42.2 kg) (yield 85%). $^1$H NMR (DMSO-$d_6$) 7.65-7.67 (m, 2H), 7.45-7.47 (m, 2H), 7.39-7.42 (m, 2H), 7.33-7.36 (m, 1H), 7.03-7.06 (m, 2H), 7.01 (d, 1H), 5.59 (t, 1H), 4.85 (t, 1H), 4.24 (t, 1H), 3.81 (s, 3H), MS (ESI): m/z 342.0 [M+H]+

Example 3

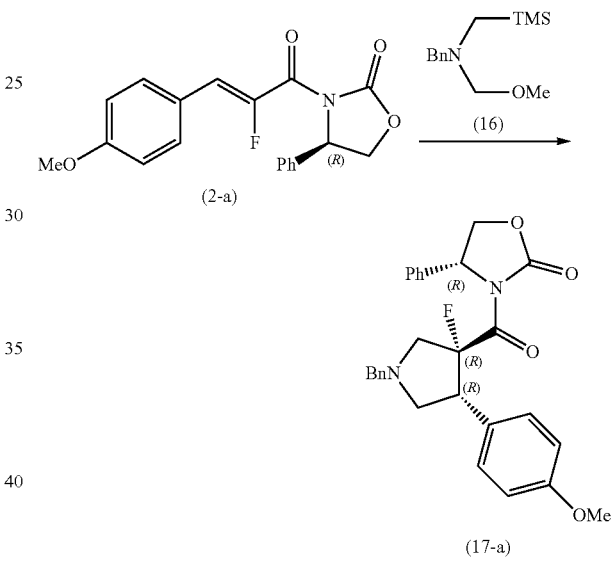

To a solution of the compound (2-a) (42.1 kg) in tetrahydrofuran (243.1 kg) were added trifluoroacetic acid (1.41 kg), the compound (16) (52.7 kg) and tetrahydrofuran (19.0 kg) in that order at room temperature, and the reaction mixture was stirred for 2 hours. Methanol (466.6 kg) was added thereto at room temperature, and the mixture was stirred at 0° C. for 30 minutes. The crystals were collected by filtration and the crystals were washed with 0° C. mixed solution of tetrahydrofuran (26.1 kg) and methanol (43.5 kg), and further with 0° C. methanol (66.5 kg). The crystals were dried at 50° C. or less to obtain the crude product of the compound (17-a). A mixture of the obtained crude product and 1,2-dimethoxyethane (164.9 kg) was stirred at 80° C. for 30 minutes, and after the mixture was cooled to 35° C., methanol (150.0 kg) was added thereto, and the mixture was stirred for 30 minutes. The crystals were collected by filtration and the crystals were washed with a mixed solution of 1,2-dimethoxyethane (36.6 kg) and methanol (33.3 kg). The crystals were dried at 50° C. or less to obtain the compound (17-a) (33.4 kg) (yield 57%). $^1$H NMR (DMSO-$d_6$) 7.29-7.42 (m, 7H), 7.23-7.29 (m, 3H), 7.17 (d, 2H), 6.82-6.85 (m, 2H), 5.42 (dd, 1H), 4.75 (dd, 1H), 4.20 (dd, 1H), 4.12 (ddd, 1H), 3.73 (s, 2H), 3.71 (s, 3H), 3.61 (dd, 1H), 3.19 (dd, 1H), 3.06 (dd, 1H), 2.83 (dd, 1H), MS (ESI): m/z 475.5 [M+H]⁺

Example 4

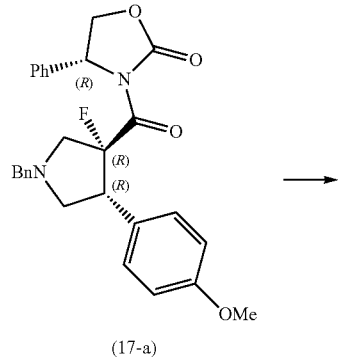

(17-a)

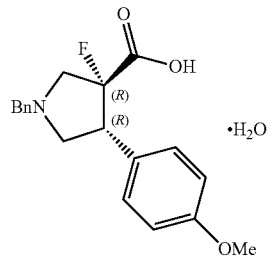

(18-a)

A solution of the compound (17-a) (33.3 kg) in tetrahydrofuran (148.0 kg) was cooled to 5° C., and a solution of lithium hydroxide monohydrate (3.53 kg) in water (33.3 kg) and water (16.7 kg) was added thereto, and the reaction mixture was stirred at 5° C. for 3.5 hours and at room temperature for 30 minutes. Thirty-five (35) % hydrochloric acid (8.68 kg) was added thereto at room temperature, and the mixture was stirred for 1 hour. The crystals were collected by filtration, and the crystals were washed with a mixed solution of tetrahydrofuran (29.6 kg) and water (10.0 kg). The crystals were dried at 50° C. or less to obtain the compound (18-a) (21.5 kg) (yield 88%). ¹H NMR (DMSO-d₆) 7.32-7.40 (m, 4H), 7.26-7.32 (m, 1H), 7.15 (d, 2H), 6.86 (d, 2H), 3.73-3.87 (m, 3H), 3.72 (s, 3H), 3.43 (ddd, 1H), 3.15 (dd, 1H), 2.90-3.10 (m, 2H), MS (ESI): m/z 330.1 [M+H]⁺

Example 5

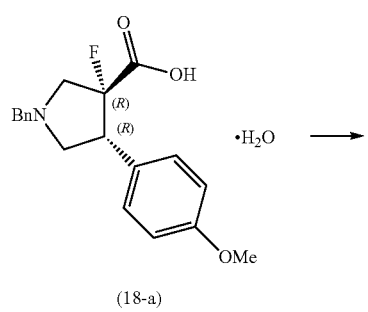

(18-a)

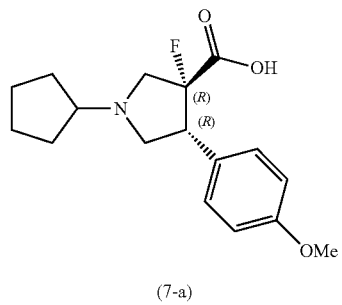

(7-a)

A mixture of methanol (126.0 kg), the compound (18-a) (21.2 kg), cyclopentanone (13.3 kg) and 10% palladium-carbon/water (2.24 kg, water content 53%) was stirred at 50° C. under a hydrogen atmosphere of 0.60 MPa for 21 hours. The reaction mixture was filtered through Celite and washed with 50° C. methanol (42.3 kg). The filtrates were concentrated at 55° C. to 42 L, and methanol (6.4 kg) was added to 64 L. After the mixture was stirred at 50° C. for 30 minutes, isopropanol (66.6 kg) was added thereto, and the mixture was stirred at 50° C. for 30 minutes and at 20° C. for 30 minutes. The crystals were collected by filtration and the crystals were washed with a mixed solution of isopropanol (22.3 kg) and methanol (11.0 kg). The crystals were dried at 60° C. or less to obtain the compound (7-a) (17.4 kg) (yield 93%). MS (APCI): m/z 308.3 [M+H]⁺

Example 6

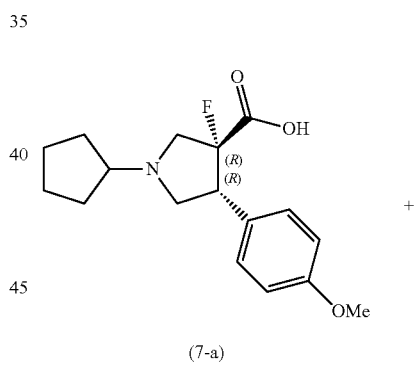

(7-a)

+

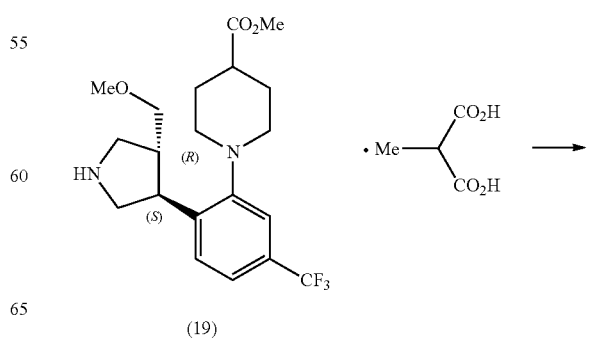

(19)

-continued

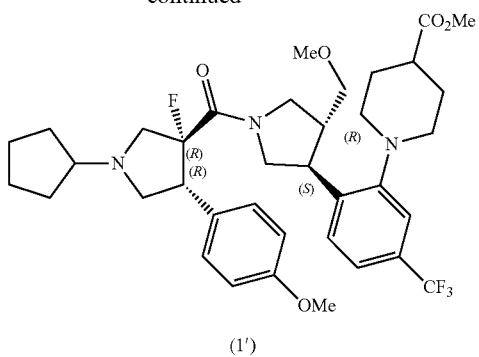

(1')

To a suspension of the compound (19) prepared according to the above-mentioned preparation examples 1 to 10 (15.2 kg) and sodium chloride (6.00 kg) in toluene (75.0 kg) were added at room temperature an aqueous solution of sodium hydrogen carbonate in water (68.8 L) and water (6.9 L) in that order, and the mixture was stirred at room temperature for 20 minutes. The aqueous layer was removed, and the organic layer was washed with water (75.7 L) and concentrated. Toluene (74.4 kg) was added thereto and the mixture was concentrated to 35 L. The mixture was diluted with toluene (22.0 kg), and the compound (7-a) (8.60 kg), N,N-diisopropylethylamine (12.7 kg) and acetonitrile (6.70 kg) were added thereto in that order at room temperature, and the mixture was stirred at room temperature for 30 minutes. The mixture was cooled to 10° C. and propylphoshonic acid anhydride (26.7 kg) was added thereto, and the reaction mixture was stirred for 13 hours. An aqueous solution of potassium carbonate (6.00 kg) in water (43.0 L), water (8.6 L) and ethyl acetate (38.8 kg) was added in that order at room temperature, and the mixture was stirred at 35° C. for 20 minutes. The aqueous layer was removed, and the organic layer was washed with an aqueous solution of citric acid monohydrate (7.70 kg) in water (51.5 L) and concentrated, and isopropanol (67.4 kg) was added thereto and then concentrated. Isopropanol (67.6 kg) was added again thereto, and concentrated to 35 L to obtain a solution of the compound (1').

Example 7

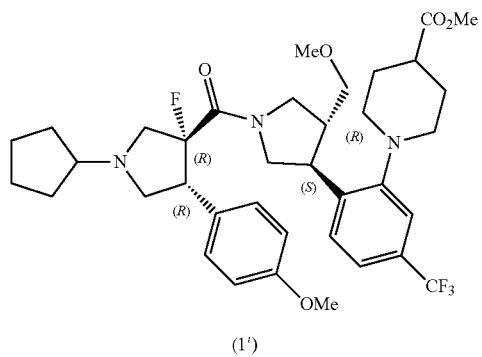

(1')

→

-continued

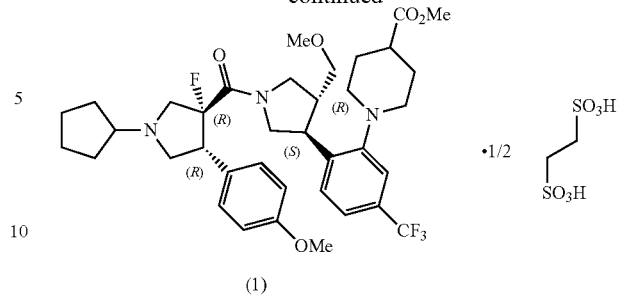

(1)

The solution of the compound (1') obtained in the Example 6 was diluted with isopropanol (13.0 kg), and an solution of 1,2-ethanedisulfonic acid hydrate (3.09 kg) in isopropanol (33.8 kg), and isopropanol (13.5 kg) were added thereto at 75° C., and the mixture was stirred at 75° C. for 1 hour and at 5° C. for 1 hour. The solids were collected by filtration, and the solids were washed with isopropanol (33.8 kg). The solids were dried at 50° C. or less to obtain the compound (1) (20.6 kg) (yield 94%). $^1$H NMR (DMSO-$d_6$) 10.50 (br d, 1H), 7.34-7.64 (m, 2H), 7.21-7.33 (m, 2H), 6.89-7.10 (m, 2H), 4.20-4.53 (m, 1H), 3.57-4.13 (m, 11H), 2.50 (m, 17H), 1.39-2.30 (m, 11H), MS (ESI): m/z 690.4 [M+H]$^+$ Next, the formed solids were collected by filtration and dried under reduced pressure. The obtained solids were subjected to a powder X-ray structural analysis, and were confirmed to be crystals (see FIG. 1).

Measuring Device: D8 DISCOVER (Bruker AXS)
  Operation Conditions
  X-ray tube: Ceramic tube, copper, tube voltage: 40 kv, tube current: 40 mA
  Incident optical system: Goebel mirror
  Photodetector: VANTEC2000
  Sample stage: UMC150 xyz
  Measuring range: 2θ=5 to 35°

The obtained crystals showed diffraction patters as indicated in Table 1 as a diffraction angle (2θ±0.2°) in the above-mentioned powder X-ray structural analysis. The compound of the present invention have the following characteristic diffraction patterns as diffraction angle (2θ±0.2°): at least 8.298, 14.198, 16.776, 17.102, 20.972, 22.658, and 24.959.

TABLE 1

| Peak No. | 2θ (°) |
|---|---|
| 1 | 8.003 |
| 2 | 8.298 |
| 3 | 9.333 |
| 4 | 11.245 |
| 5 | 11.930 |
| 6 | 11.964 |
| 7 | 12.459 |
| 8 | 13.460 |
| 9 | 13.772 |
| 10 | 13.774 |
| 11 | 14.198 |
| 12 | 15.437 |
| 13 | 15.962 |
| 14 | 16.180 |
| 15 | 16.776 |
| 16 | 17.102 |
| 17 | 17.427 |
| 18 | 17.687 |
| 19 | 18.704 |
| 20 | 19.538 |

23

TABLE 1-continued

| Peak No. | 2θ (°) |
|---|---|
| 21 | 19.646 |
| 22 | 20.439 |
| 23 | 20.972 |
| 24 | 21.522 |
| 25 | 22.658 |
| 26 | 23.378 |
| 27 | 24.065 |
| 28 | 24.450 |
| 29 | 24.959 |
| 30 | 25.344 |
| 31 | 26.275 |
| 32 | 26.881 |

Alternative Method of Example 7

To a solution of the compound (1') (276 mg) in ethanol (1.4 mL) was added 1,2-ethanedisulfonic acid hydrate (38 mg), and the mixture was stirred at room temperature for 40 minutes. The crystals were collected by filtration, and the crystals were washed with ethanol (0.84 mL) twice. The crystals were dried at 40° C. or less to obtain the compound (1) (178 mg) (yield 57%), and an elemental analysis of the crystals were measured.

TABLE 2

|  | C | H | N | F | S |
|---|---|---|---|---|---|
| Theoretical value of compound (1) | 58.15 | 6.42 | 5.35 | 9.68 | 4.08 |
| Measured value of Crystal | 57.00 | 6.40 | 5.22 | 9.49 | 4.03 |

Example 8

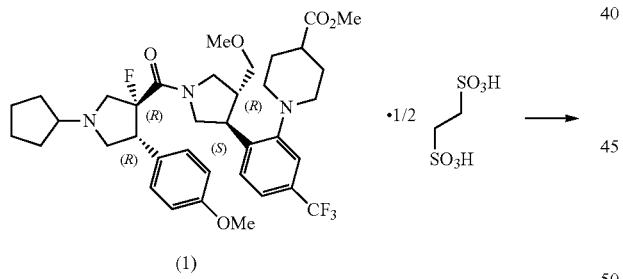

To a suspension of the compound (1) (19.3 kg) in ethyl acetate (86.6 kg) were added at room temperature a solution of potassium carbonate (3.40 kg) in water (77.0 L) and water (19.3 L) in that order, and the mixture was stirred at room temperature for 20 minutes. The aqueous layer was removed, and the organic layer was washed with water (96.3 L) twice, and concentrated to 35 L. Ethanol (75.9 kg) was added thereto, and the mixture was concentrated to 35 L. Ethanol (45.4 kg) was added thereto, and insoluble materials were filtered off, and ethanol (30.2 kg) was added thereto, and the mixtures were concentrated to 35 L. The mixture was diluted with ethanol (17.9 kg) to 58 L, and 24% aqueous sodium hydroxide solution (6.1 kg) and water (15.6 kg) were added in that order at room temperature, and the mixture was stirred for 5 hours at room temperature to obtain the compound (11). MS (ESI): m/z 676.6 [M+H]$^+$ Alternative Method of Example 8

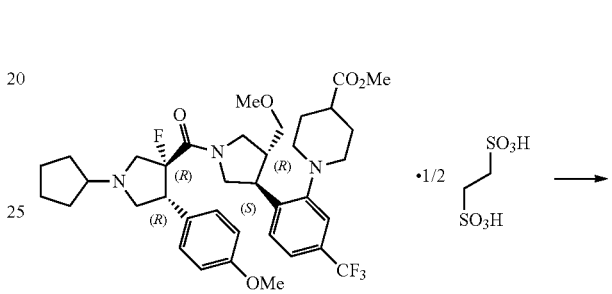

To a suspension of the compound (1) (37.1 kg) in ethyl acetate (167.5 kg) were added at room temperature an aqueous solution of potassium carbonate (6.5 kg) in water (148.3 L) and water (36.8 L) in that order, and the mixture was stirred at room temperature for 15 minutes. The aqueous layer was removed, and the organic layer was washed with water (186 L) twice, and ethyl acetate (67.2 kg) was added thereto, and insoluble materials were filtered off. The filtrates were concentrated to 78 L, and ethanol (146.5 kg) was added thereto, and the mixture was concentrated to 78 L. Ethanol (146.9 kg) was added thereto, and the mixture was concentrated to 56 L. The mixture was diluted with ethanol (44 kg) and 24% aqueous sodium hydroxide solution (8.7 kg) and water (30.1 kg) were added in that order at room temperature, and the mixture was stirred at 40° C. for 5 hours to obtain the compound (11).

Next, the preparation example of the compound (19) described in Example 6 is shown.

Preparation Example 1

Preparation Example 2

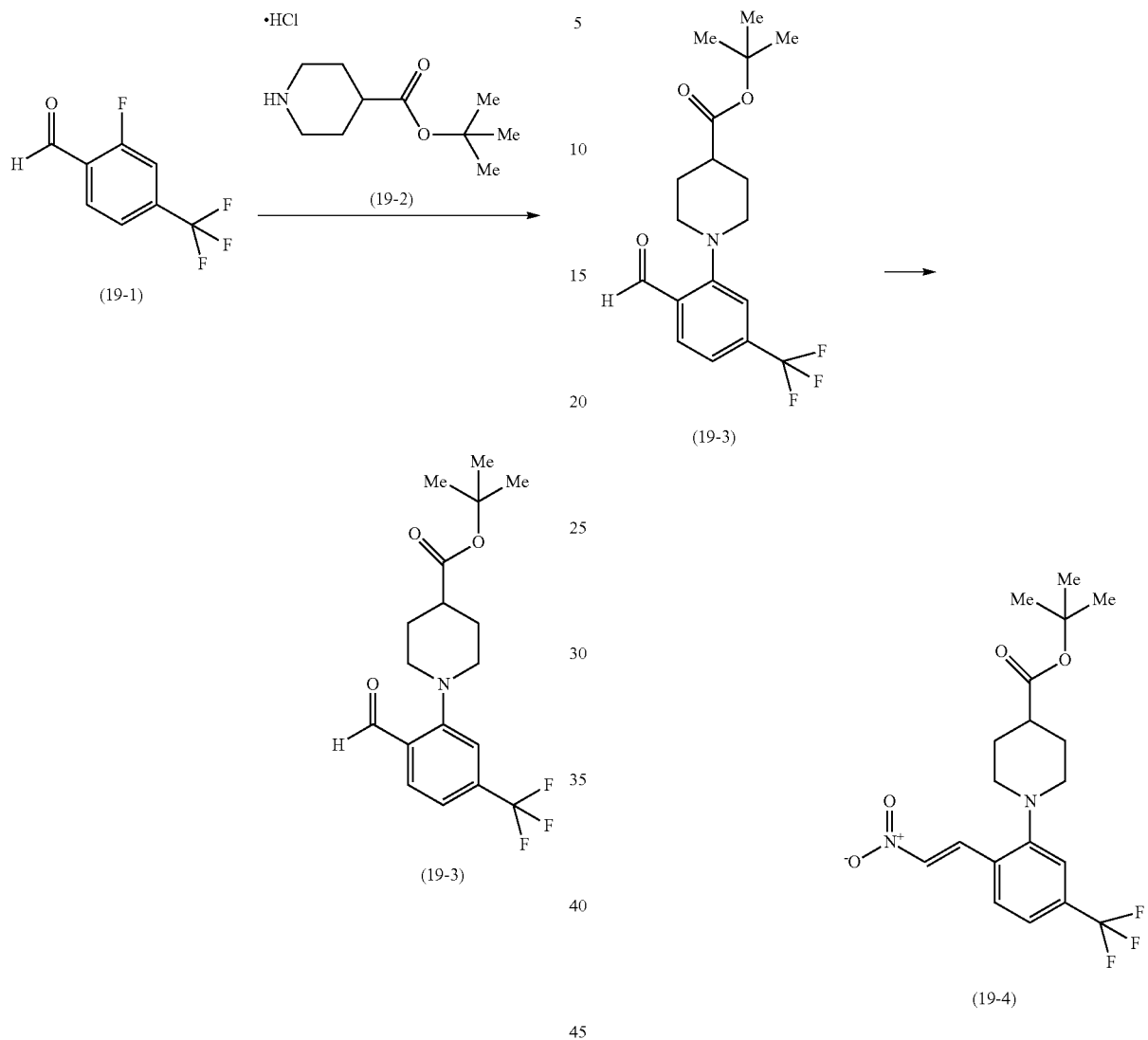

Potassium carbonate (26.1 kg) was dissolved in water (101.5 L), and the compound (19-2) (18.4 kg), toluene (75.2 kg) and the compound (19-1) (14.8 kg) were added thereto in that order at room temperature, and the reaction mixture was stirred at 85° C. for 22 hours. After the mixture was cooled to 40° C., the organic layer was collected by separating the mixture with a separatory funnel, and water (101.5 L) and citric acid monohydrate (14.5 kg) were added thereto at room temperature, and the mixture was stirred. To the organic layer collected by separating with a separatory funnel was added water (101.5 L) at room temperature, and the mixture was stirred, and the organic layer collected by separating with a separatory funnel was concentrated at 50° C. to 60 L. Toluene (47.7 g) was added the concentrated residue, and the mixture was concentrated at 50° C. to 30 L to obtain the compound (19-3).

To a solution (30 L) of the compound (19-3) obtained in the Preparation Example 1 were added at room temperature nitromethane (47.0 kg), toluene (12.8 kg) and 28% solution (0.45 kg) of sodium methoxide in methanol in that order, and the reaction mixture was stirred for 4 hours. The mixture was cooled to −5° C., and toluene (102.3 kg), methanesulfonyl chloride (13.2 kg) and triethylamine (17.1 kg) were added in that order, and the mixture was stirred for 1 hour. Water (29.7 L) was added thereto at room temperature, and the mixture was stirred, and the organic layer collected by separating with a separatory funnel was concentrated at 50° C. to 120 L. Toluene (79.5 kg) was added to the concentrated residue, and the mixture was concentrated at 50° C. to 120 L. Toluene (77.0 kg) was added to the concentrated residue again, and the mixture was concentrated at 50° C. to 120 L to obtain a solution of the compound (19-4).

Preparation Example 3

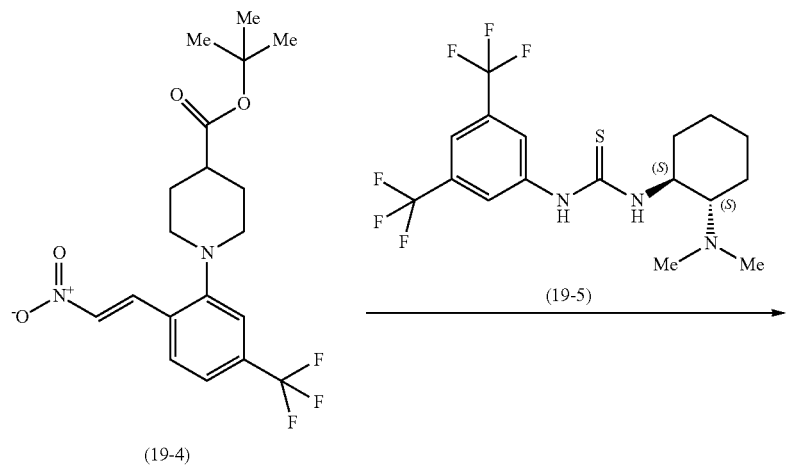
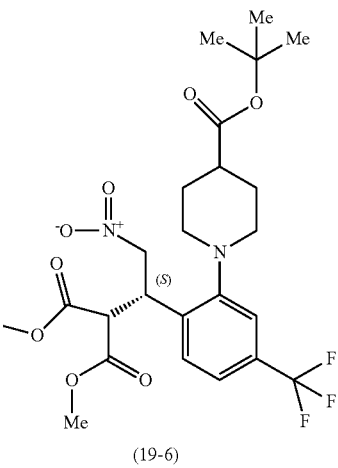

To a solution (120 L) of the compound (19-4) obtained in the Preparation Example 2 were added at room temperature water (29.6 L), sodium hydrogen carbonate (2.96 kg) and dimethyl malonate (17.3 kg) and the compound (19-5) (0.95 kg) in that order, and the reaction mixture was stirred for 19 hours. The organic layer was collected at 45° C. by separating with a separatory funnel, and concentrated at 50° C. to 60 L. 2-Propanol (92.7 kg) was added to the concentrated residue, and the mixture was concentrated at 65° C. to 90 L. 2-Propanol (93.5 kg) was added to the concentrated residue again, and the mixture was concentrated at 65° C. to 90 L. After the mixture was cooled to 25° C., the mixture was stirred for 16 hours. Further, after the mixture was cooled to −9° C. and stirred for 2 hours, the crude crystals were collected by filtration, and washed with water (147.8 L). The crude crystals were dissolved in 1,2-dimethoxyethane (106.3 kg) at room temperature, and the mixture was concentrated at 50° C. to 50 L. 1,2-Dimethoxyethane (107.0 kg) was added to the concentrated residue, and the mixture was concentrated at 50° C. to 50 L. 1,2-Dimethoxyethane (106.2 kg) was added to the concentrated residue again, and the mixture was concentrated at 50° C. to 50 L to obtain a solution of the compound (19-6).

Preparation Example 4

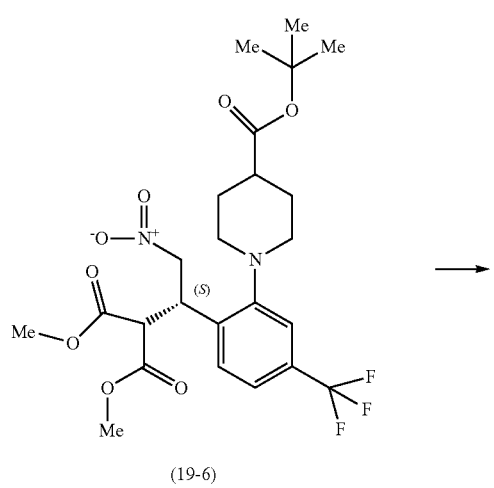

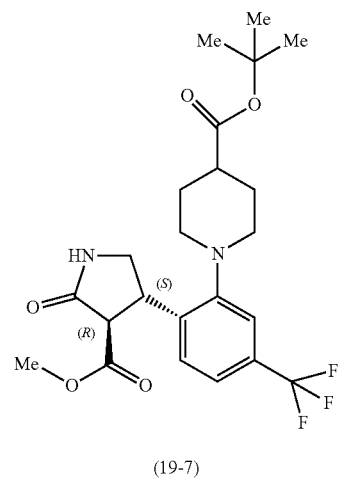

To a solution (50 L) of the compound (19-6) obtained in the Preparation Example 3 were added at room temperature 1,2-dimethoxyethane (91.6 kg), 5% rhodium-carbon (water content 56.3%, 10.6 kg) and acetic acid (2.99 kg) in that order, and the reaction mixture was pressurized (0.6 MPa) with hydrogen gas at 60° C., and the mixture was stirred for 20 hours. After the mixture was cooled to 25° C., the solids in the reaction mixture were filtered off to obtain the filtrates. The filtered residues were washed with 1,2-dimethoxyethane (114.8 kg), and the washed solutions were combined with the filtrates, and the mixture was concentrated at 50° C. to 60 L. 1,2-Dimethoxyethane (115.0 kg) was added to the concentrated residues, and mixture was concentrated at 50° C. to 53 L. 1,2-Dimethoxyethane (114.9 kg) was added to the concentrated residues again, and the mixture was concentrated at 50° C. to 53 L. The concentrated residues were cooled to room temperature, and 1,2-dimethoxyethane (11.5 kg) was added thereto to obtain the concentrated solution of the compound (19-7). The concentrated solution was mixed with the concentrated solution (scale 1.0 time) of the compound (19-7) which was similarly prepared according to the above-mentioned operations, and 1,2-dimethoxyethane (69.1 kg) was added thereto. The mixture was concentrated at 50° C. to 110 L, and methanol (6.76 kg) and 1,2- dimethoxyethane (48.8 kg) were added thereto at room temperature in that order to obtain a solution (179 L) of the compound (19-7).

Preparation Example 5

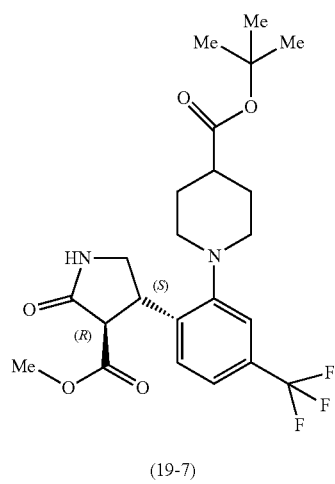

(19-7)

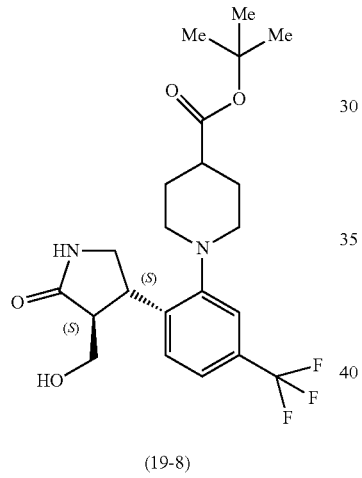

(19-8)

To a suspension of sodium borohydride (7.99 kg) in 1,2-dimethoxyethane (146.7 kg) were added at 45° C. the solution of the compound (19-7) prepared in Preparation Example 4 and 1,2-dimethoxyethane (49.1 kg) in that order, and the reaction mixture was stirred for 1 hour, and then cooled to room temperature. This reaction solution and 1,2-dimethoxyethane (25.0 kg) were added at 25° C. to an aqueous solution of ammonium chloride (45.2 kg) in water (169.0 kg) in that order. Ethyl acetate (235.7 kg) was added thereto at room temperature, and the mixture was stirred. The organic layer was collected by separating with a separatory funnel, and water (112.3 L) was added thereto at room temperature, and the mixture was stirred, and the organic layer that was collected by separating with a separatory funnel was concentrated at 50° C. to 170 L. Ethyl acetate (253.7 kg) was added to the concentrated residue and the mixture was concentrated at 50° C. to 170 L. Heptane (231.5 L) was added thereto at 50° C., and the mixture was stirred for 0.7 hours, and then cooled to 10° C., and stirred for 15 hours. The crystals were collected by filtration, and the crystals were washed with mixed solution of ethyl acetate (25.6 kg) and heptane (58.0 kg) that was cooled to 10° C., and further with room temperature water (112.4 L). The crystals were dried at 50° C. to obtain the compound (19-8) (30.2 kg) (yield 44% based on the compound (19-1)).

Preparation Example 6

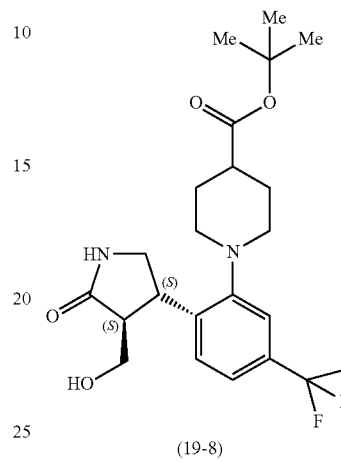

(19-8)

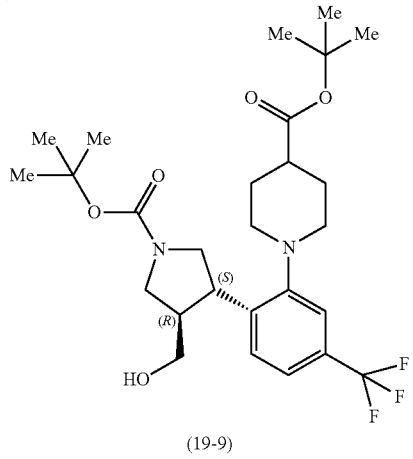

(19-9)

To a solution of the compound (19-8) (29.0 kg) in 1,2-dimethoxyethane (163.6 kg) was added at 10° C. a solution of methyl trifluoromethane sulfonate (16.1 kg) in 1,2-dimethoxyethane solution (87.9 kg), and the reaction mixture was stirred for 2 hours. After sodium tetrahydroborate (2.5 kg) was added at 0° C. to the reaction mixture, the mixture was stirred at 10° C. for 2 hours. After triethylamine (16.6 kg) was added thereto, a solution of di-tert-butyl dicarbonate (13.6 kg) in 1,2-dimethoxyethane (25.0 kg) was added thereto, and the mixture was stirred for 2 hours. The mixture was further stirred at 45° C. for 2 hours, and then cooled to 25° C. Toluene (175.7 kg) was added thereto, and the organic layer was collected by separating with a separatory funnel, and an aqueous solution of ammonium chloride (20.3 kg) in water (182.7 L) was added thereto, and the organic layer was collected by separating with a separatory funnel. Next, the organic layer was washed with an aqueous solution of sodium hydrogen carbonate (5.8 kg) in water (110.2 L) and concentrated to 104 L to obtain the compound (19-9).

Preparation Example 7

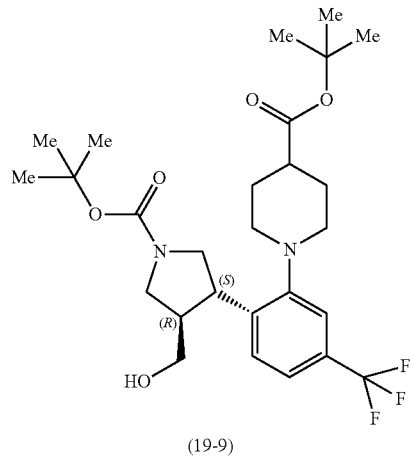

(19-9)

To a suspension of N,N-dimethylformamide (97.9 kg), sodium hydroxide (15.7 kg) and toluene (18.0 kg) were added at −10° C. iodomethane (37.2 kg), N,N-dimethylformamide (13.1 kg), and the solution of compound (19-9) obtained in the Preparation Example 6 (104 L) in that order, and the reaction mixture was stirred at 0° C. for 10 hours. Water (117.6 L), triethylamine (26.5 kg), and toluene (90.0 kg) were added thereto, and the organic layer was collected by separating with a separatory funnel. The organic layer was washed with an aqueous solution of ammonium chloride (41.5 kg) in water (373.7 L) twice, and successively with an aqueous solution of sodium hydrogen carbonate (10.4 kg) in water (197.2 L) to obtain a solution of the compound (19-10).

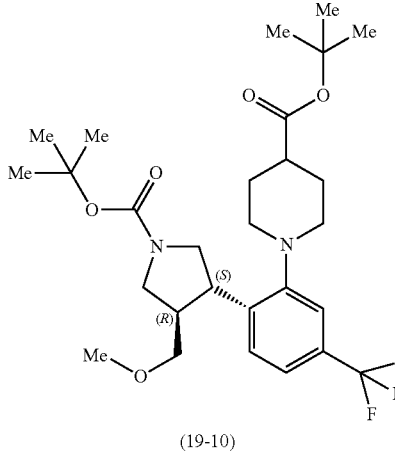

(19-10)

Preparation Example 8

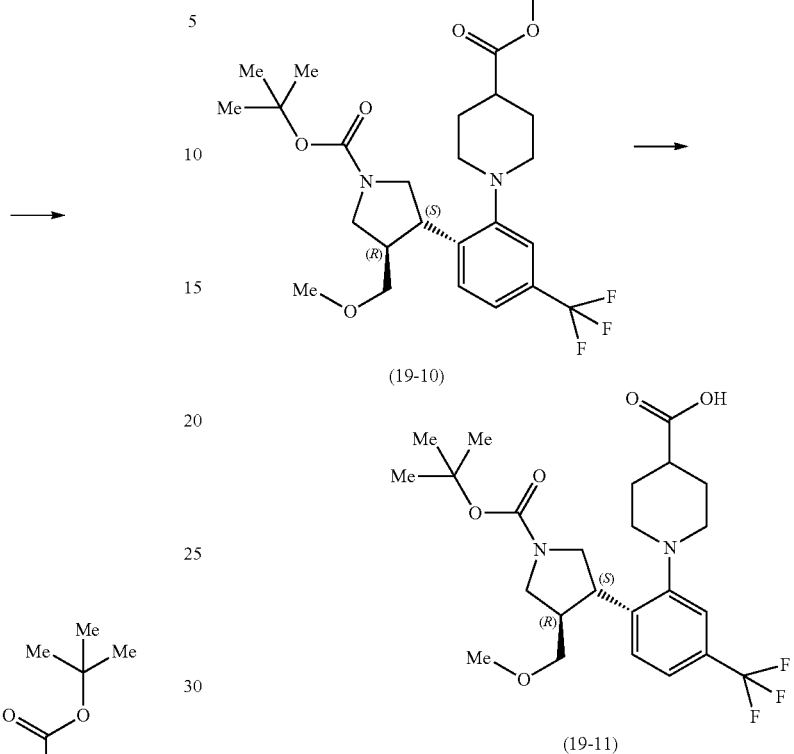

(19-10)

(19-11)

To the whole amount of the solution of compound (19-10) obtained in the Preparation Example 7 was added at 40° C. a solution of potassium hydroxide (17.3 kg) in methanol (213.6 L), and the mixture was stirred at 65° C. for 18 hours. The mixture was cooled to 50° C., and water (106.8 L) ad heptane (121.8 kg) were added thereto, and the aqueous layer was collected by separating with a separatory funnel. An aqueous solution of methanol (10.7 L) in water (7.1 L) and toluene (110.4 kg) were added thereto in that order. An aqueous solution of concentrated hydrochloric acid (39.8 kg) in water (159.7 L) was added thereto at 10° C., and the mixture was stirred and the organic layer was then collected by separating with a separatory funnel to obtain the compound (19-11).

Preparation Example 9

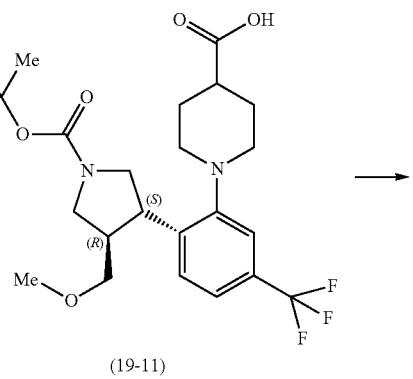

(19-11)

-continued

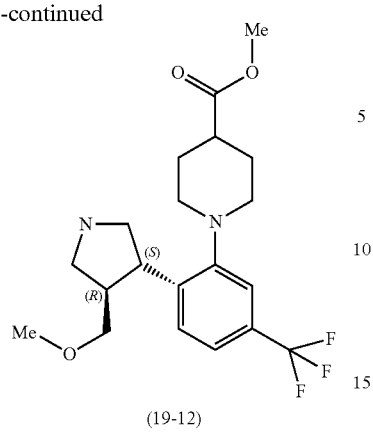

(19-12)

Acetyl chloride (41.2 kg) was added at −10° C. to methanol (127.6 L), and then the whole amount of the solution of compound (19-11) obtained in the Preparation Example 8 and the methanol (16.0 L) were added dropwise thereto at 15° C. The reaction mixture was stirred at 20° C. for 4 hours, and methanol (16.0 L) was added thereto. Twenty-four (24) % aqueous sodium hydroxide solution (80.9 kg), water (129.8 L) and an aqueous solution of sodium carbonate (13.9 kg) in water (127.7 L) were added thereto in that order, and the mixture was stirred while mixing, and the organic layer was collected by separating with a separatory funnel. The organic layer was washed with an aqueous solution of sodium chloride (9.6 kg) in water (95.7 L) to obtain a solution of the compound (19-12).

Preparation Example 10

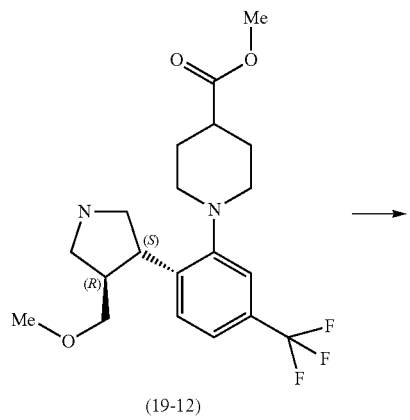

(19-12)

→

-continued

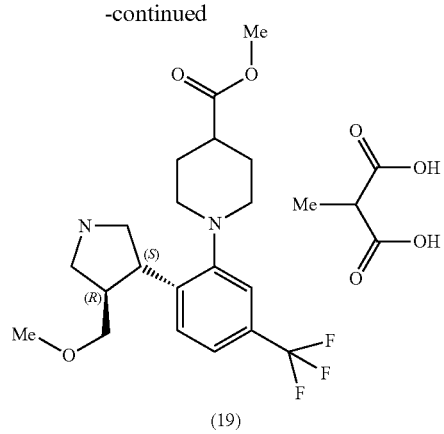

(19)

To the solution of compound (19-12) obtained in the Preparation Example 9 were added toluene (55.2 kg), ethanol (75.6 kg) and 2-methyl malonate (4.9 kg), and the reaction mixture was stirred at 15° C. to 8° C. for 8 hours. The crystals were collected by filtration, and washed with a solution of ethanol (12.4 kg) in toluene (27.8 kg) that was cooled to 8° C., and dried at 50° C. to obtain the compound (19) (15.3 kg) (yield 45% based on the compound (19-8)).

Example 1 of Experiment

The compound (1') (20 mg) was dissolved in various kinds of organic solvents (100 μL), and any acid as indicated in Table 1 (molar equivalent ratio: 1) was added, and the completedly dissolved samples were left to stand. The results are shown in Table 3 below. As shown in Table 3, only in the case of the combination of 1,2-ethanedisulfonic acid dihydrate and ethanol, only solids could be obtained among the studied conditions.

TABLE 3

| Acid | Solvent | | | | | | | |
|---|---|---|---|---|---|---|---|---|
| | Methyl ter-butyl ether | 2-Methyl-tetra-hydrofuran | Ethanol | 1,2-Dimethoxy-ethane | Isopropyl acetate | Tetra-hydrofuran | Methyl isopropyl ketone | Acetonitrile |
| 2M Hydrochloric acid/ methanol | x | x | x | — | — | — | — | — |
| Phosphoric acid | x | x | x | — | — | — | — | — |

TABLE 3-continued

| Acid | Solvent | | | | | | | |
|---|---|---|---|---|---|---|---|---|
| | Methyl ter-butyl ether | 2-Methyl-tetra-hydrofuran | Ethanol | 1,2-Dimethoxy-ethane | Isopropyl acetate | Tetra-hydrofuran | Methyl isopropyl ketone | Acetonitrile |
| Sulfuric acid | x | x | x | — | — | — | — | — |
| Maleic acid | x | x | x | — | — | — | — | — |
| Fumaric acid | — | x | x | — | — | — | — | — |
| Citric acid monohydrate | x | x | x | — | — | — | — | — |
| L-tartaric acid | — | x | x | — | — | — | — | — |
| Malonic acid | — | x | x | — | — | — | — | — |
| (+)-Camphor acid | — | x | x | — | — | — | — | — |
| (+)-Dibenzoyl-D-tartaric acid monohydrate | x | x | x | — | — | — | — | — |
| 1,5-Naphthalene disulfonic acid | — | — | x | — | — | — | — | — |
| (−)-Camphor-sulfonic acid | — | x | x | — | — | — | — | — |
| Methane-sulfonic acid | — | x | x | — | — | — | — | — |
| 1,2-Etanedi-sulfonic acid dihydrate | — | x | o | x | x | x | x | x |

In the Table, "-" means that an acid was not dissolved, or the study wasn't conducted, "x" means that only solids couldn't be obtained, and "o" means that only solids could be obtained.

Example 2 of Experiment

With respect to the below-mentioned compound (2-a), compound (20-a) and compound (21-a), as shown in Examples 2-1 to 2-3, the cyclization of these compounds with the compound (16) was conducted, and the stereoselectivity of the products were compared.

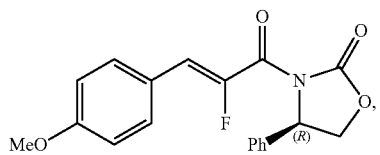
(2-a)

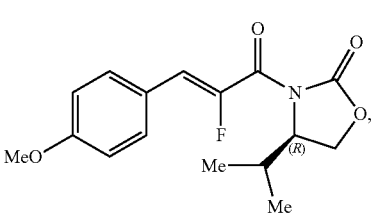
(20-a)

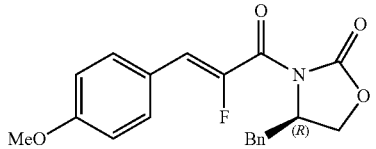
(21-a)

Example 2-1 of Experiment

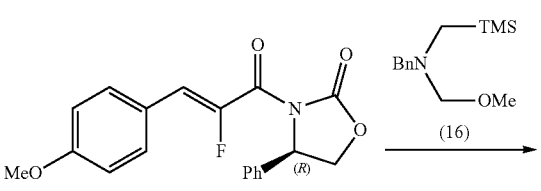

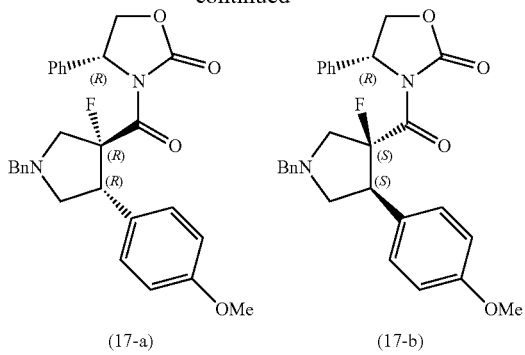

(17-a)   (17-b)

To a suspension of the compound (2-a) (6.75 g) in dichloromethane (30 mL) were added at room temperature a solution of compound (16) (14.1 g) in dichloromethane (30.0 mL) and trifluoroacetic acid (0.152 mL) in that order, and the reaction mixture was stirred for 30 minutes under heat reflux. The mixture was stood to cool to room temperature, and an ice-cooled aqueous citric acid (25.0 g) in water (250 mL) was added thereto, and the mixture was extracted with chloroform (100 mL) twice. The organic layer was washed with saturated aqueous sodium hydrogen carbonate solution and dried over anhydrous magnesium sulfate. The drying agent was removed, and the solvents were evaporated under reduced pressure. The resulting residues were triturated with isopropyl ether to obtain a mixture of the compound (17-a) and the compound (17-b) (7.39 g) (yield 79%). The diastereomer ratio in the obtained mixture was measured with NMR analysis, and as a result, the ratio was that of the compound (17-a):the compound (17-b)=5.1:1.

Example 2-2 of Experiment

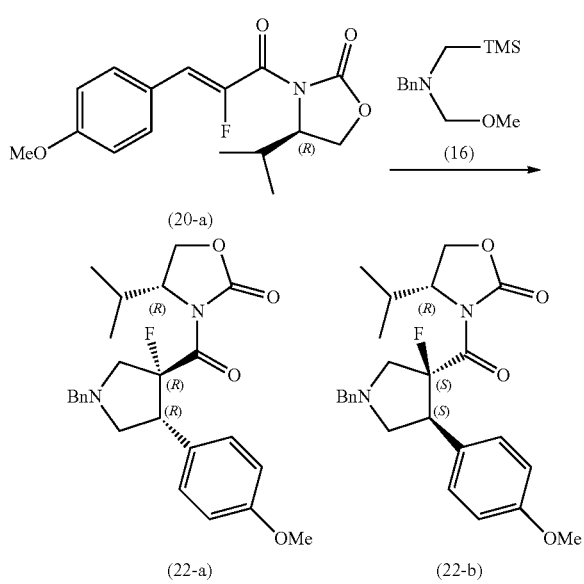

(22-a)   (22-b)

To a solution of the compound (20-a) (928 mg) and the compound (16) (2.15 g) in dichloromethane (9.0 mL) was added at room temperature trifluoroacetic acid (0.023 mL), and the reaction mixture was stirred under heat reflux. The mixture was stood to cool to room temperature, and an aqueous solution of citric acid (3.0 g) in water (30 mL) was added thereto under ice-cooling, and the mixture was extracted with chloroform. The organic layer was washed with saturated aqueous sodium hydrogen carbonate solution, and dried over anhydrous magnesium sulfate. The drying agent was removed and the solvents were evaporated under reduced pressure. The resulting residues were purified by silica gel chromatography (hexane:ethyl acetate=9:1 to 2:1) to obtain a compound (22-a) (588 mg) (yield 44%) and a compound (22-b) (253 mg) (yield 19%). The diastereomer ratio was that of the compound (22-a):the compound (22-b)=2.3:1.

Example 2-3 of Experiment

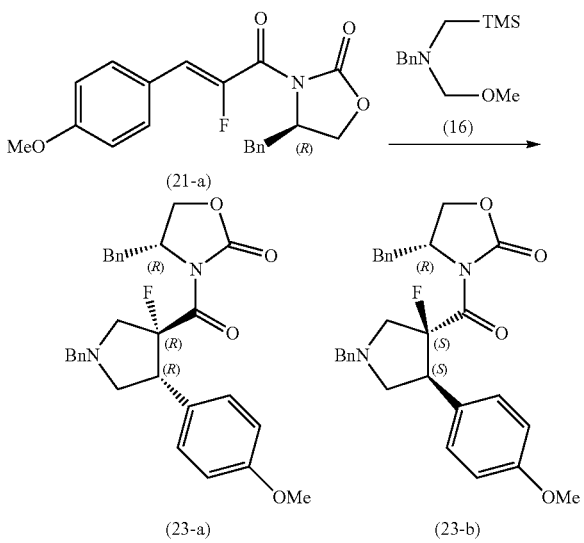

(23-a)   (23-b)

To a mixture of the compound (21-a) (34.7 g), the compound (16) (58.0 g) and chloroform (200 mL) was added at room temperature trifluoroacetic acid (0.940 mL), and the reaction mixture was stirred at room temperature for 30 minutes and under heat reflux for 30 minutes. The mixture was stood to cool to room temperature, and the compound (14) (11.6 g) and trifluoroacetic acid (0.188 mL) were added thereto, and the reaction mixture was stirred under heat reflux for 30 minutes. The mixture was stood to cool to room temperature, and an aqueous solution of ice-cooled citric acid (100 g) in water (1.00 L), and the aqueous layer was removed. The organic layer was washed with saturated aqueous sodium hydrogen carbonate solution, and dried over anhydrous magnesium sulfate. The drying agent was removed, and the solvents were evaporated under reduced pressure. The resulting residues were triturated with diisopropyl ether (150 mL) to obtain a mixture of a compound (23-a) and a compound (23-b) (35.5 g). The resulting mixture was purified by silica gel chromatography (hexane:ethyl acetate=4:1 to 1:1) to obtain the compound (23-a) (20.3 g) (yield 43%) and the compound (23-b) (10.5 g) (yield 22%). The diastereomer ratio was that of the compound (23-a):the compound (23-b)=1.9:1.

As a result of the above-mentioned Examples 2-1 to 2-3, the diastereomer ratio of the reaction products was shown in Table 4, and it was thus found that the reaction of the compound (2-a) with the compound (16) which was described in Example 2-1 showed the highest stereoselectivity. Namely, it was found that the compound (17-a) as an intermediate compound for the compound of the present invention, which is described in Example 3 can be obtained effectively in terms of stereoselectivity.

TABLE 4

| Example No. | Compound to be reacted with compound (16) | Diastereomer ratio of Product |
| --- | --- | --- |
| 2-1 | Compound (2-a) | 5.1:1 |
| 2-2 | Compound (20-a) | 2.3:1 |
| 2-3 | Compound (21-a) | 1.9:1 |

INDUSTRIAL APPLICABILITY

The compound of the present invention has excellent crystallinity and can be thus applied as an intermediate compound for a compound that is useful for prophylaxis or treatment of various diseases or conditions in which an activation of melanocortin receptor is involved. Also the method of the present invention can be applied as a method showing excellent stereoselectivity for preparing the compound of the present invention, and as a result, can be applied as a method showing excellent stereoselectivity for preparing compound that is useful for prophylaxis or treatment of various diseases or conditions in which an activation of melanocortin receptor is involved.

The invention claimed is:

1. Methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid, which is represented by formula (1):

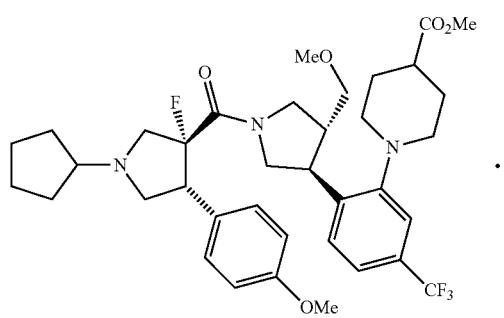

2. A 1/2 ethane-1,2-disulfonic acid salt of a compound (1'):

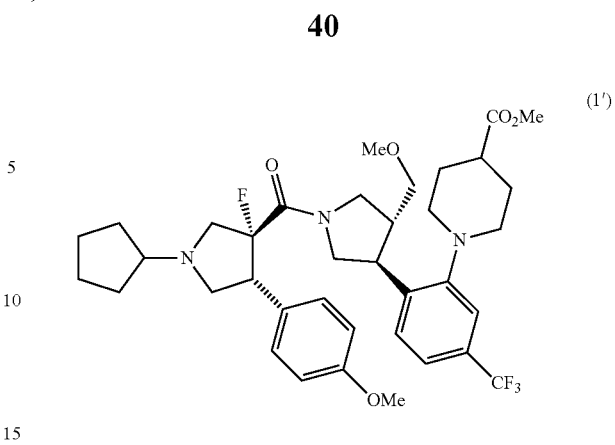

wherein the compound is in crystalline form.

3. A method for preparing a compound represented by formula (11):

or a pharmaceutically acceptable salt thereof, which comprises a step of hydrolyzing methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid to provide a compound of formula (11), and optionally, further converting the compound of formula (11) to a salt thereof.

4. A method for making methyl 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylate 1/2 ethane-1,2-disulfonic acid which is shown by the following reaction scheme:

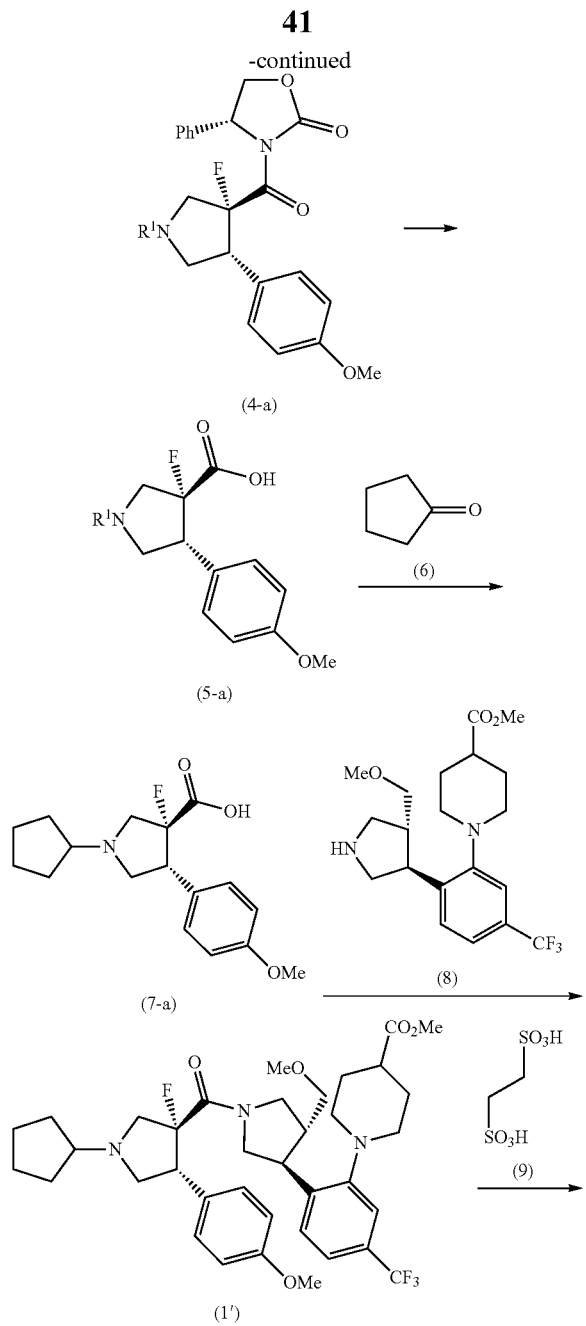

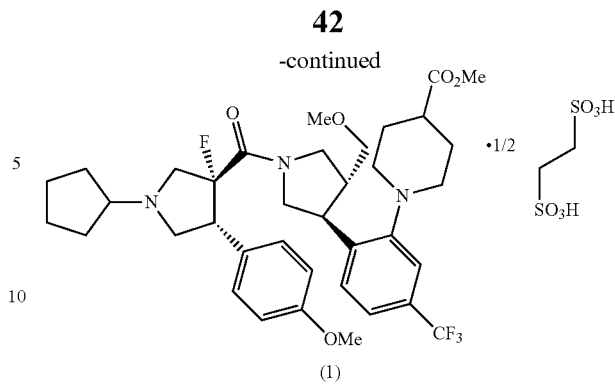

wherein
R[1] represents a protecting group for an amino group which is an alkyl having one to six carbon atoms which may be optionally substituted with aryl in which the aryl may be optionally substituted with alkoxy having one to six carbon atoms, R[2] represents a silyl which is substituted with one to three alkyl having one to six carbon atoms or a cyano, and R[3] represents an alkoxy having one to six carbon atoms, wherein the method comprises the following steps:

(a) a step of reacting a compound (2-a) with a compound (3) to obtain a compound (4-a) or a salt thereof, (b) a step of hydrolyzing the compound (4-a) or a salt thereof to obtain a compound (5-a) or a salt thereof, (c) a step of removing a protecting group R[1] of an amino group in the compound (5-a) or a salt thereof, followed by reacting with a compound (6) to obtain a compound (7-a) or a salt thereof, (d) a step of condensing the compound (7-a) or a salt thereof with a compound (8) or a salt thereof to obtain a compound (1') or a salt thereof, and (e) a step of reacting the compound (1'), or the compound (1') which is obtained by desalting of a salt of the compound (1'), with a compound (9) to obtain a compound (1).

5. The method according to claim 4, wherein R[1] represents a benzyl, R[2] represents a trimethylsilyl, and R[3] represents a methoxy.

* * * * *